(12) United States Patent
Hyde et al.

(10) Patent No.: US 10,335,086 B2
(45) Date of Patent: *Jul. 2, 2019

(54) ITEM ATTACHABLE TO A SUBJECT AND INCLUDING A SENSOR FOR SENSING AN OBJECT THAT A BODY PORTION OF THE SUBJECT MAY CONTACT

(71) Applicant: ELWHA LLC, Bellevue, WA (US)

(72) Inventors: Roderick A. Hyde, Redmond, WA (US); Muriel Y. Ishikawa, Livermore, CA (US); Jordin T. Kare, San Jose, CA (US); Eric C. Leuthardt, St. Louis, MO (US); Mark A. Malamud, Seattle, WA (US); Tony S. Pan, Bellevue, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,313

(22) Filed: Feb. 27, 2015

(65) Prior Publication Data

US 2016/0249855 A1 Sep. 1, 2016

(51) Int. Cl.
*A61B 5/00* (2006.01)
*A61B 5/11* (2006.01)
*G01S 13/93* (2006.01)

(52) U.S. Cl.
CPC .......... *A61B 5/6829* (2013.01); *A61B 5/1122* (2013.01); *A61B 5/6807* (2013.01);
(Continued)

(58) Field of Classification Search
None
See application file for complete search history.

(56) References Cited

U.S. PATENT DOCUMENTS 7,242,817 B2 7/2007 Takeda et al.
7,610,688 B2 11/2009 Yun
(Continued)

OTHER PUBLICATIONS

Dae-Hyeong Kim and John A. Rogers; "Stretchable Electronics: Materials Strategies and Devices", in Advanced Materials; 2008, 20, 4887-4892.

*Primary Examiner* — Leon-Viet Nguyen
(74) *Attorney, Agent, or Firm* — Fogg & Powers LLC

(57) ABSTRACT

An embodiment of a device includes at least one sensor, a determiner, and a notifier. The at least one sensor is configured to be located on a body portion of a subject and to sense an object. The determiner is configured to determine, in response to the sensor, whether the body portion may contact the object. The notifier is configured to notify the subject in response to the determiner determining that the body portion may contact the object. Such a device (e.g., attached to, or part of, a shoe) may be useful to warn a subject of a potential collision between an object (e.g., stairs, furniture, door jamb, curb, toy) and a body part (e.g., foot, toes) in which the subject has lost feeling, the ability to feel pain, or proprioception. And such a warning may help the subject to avoid inadvertently and repeatedly injuring the body part.

34 Claims, 19 Drawing Sheets

(52) U.S. Cl.
CPC ............ *G01S 13/93* (2013.01); *A61B 5/4824* (2013.01); *A61B 5/6803* (2013.01); *A61B 5/6805* (2013.01); *A61B 5/6806* (2013.01); *A61B 5/6822* (2013.01); *A61B 5/6828* (2013.01); *A61B 5/746* (2013.01); *A61B 2560/0214* (2013.01); *A61B 2562/0219* (2013.01); *G01S 2013/9364* (2013.01); *G01S 2013/9367* (2013.01)

(56) References Cited

U.S. PATENT DOCUMENTS

| | | | |
|---|---|---|---|
| 7,771,371 B2 | 8/2010 | Avni | |
| 8,006,795 B2 | 8/2011 | Manor | |
| 8,421,822 B2 | 4/2013 | Odland et al. | |
| 2004/0031169 A1 | 2/2004 | Jensen et al. | |
| 2006/0267779 A1* | 11/2006 | Ishikawa | A41D 13/018 340/573.1 |
| 2007/0173903 A1 | 7/2007 | Goren et al. | |
| 2008/0093144 A1 | 4/2008 | Manor | |
| 2009/0237233 A1* | 9/2009 | Smith | G08B 6/00 340/539.1 |
| 2010/0002402 A1 | 1/2010 | Rogers et al. | |
| 2010/0152619 A1 | 6/2010 | Kalpaxis et al. | |
| 2010/0289971 A1 | 11/2010 | Odland et al. | |
| 2012/0119920 A1* | 5/2012 | Sallop | A43B 3/0005 340/686.6 |
| 2012/0151800 A1 | 6/2012 | Woods | |
| 2012/0276999 A1 | 11/2012 | Kalpaxis et al. | |
| 2013/0000156 A1 | 1/2013 | Andoh | |
| 2013/0192071 A1 | 8/2013 | Esposito et al. | |
| 2014/0118498 A1* | 5/2014 | Lee | A43B 3/0005 348/46 |
| 2014/0132388 A1* | 5/2014 | Alalawi | G09B 21/003 340/4.12 |
| 2014/0216524 A1 | 8/2014 | Rogers et al. | |
| 2016/0082885 A1* | 3/2016 | Rashid | B60Q 9/008 340/435 |

* cited by examiner

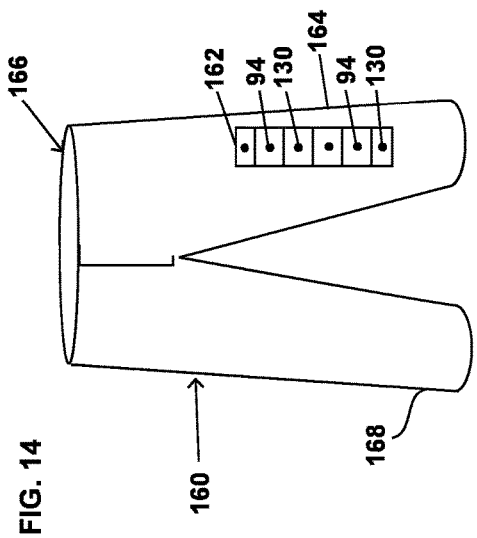
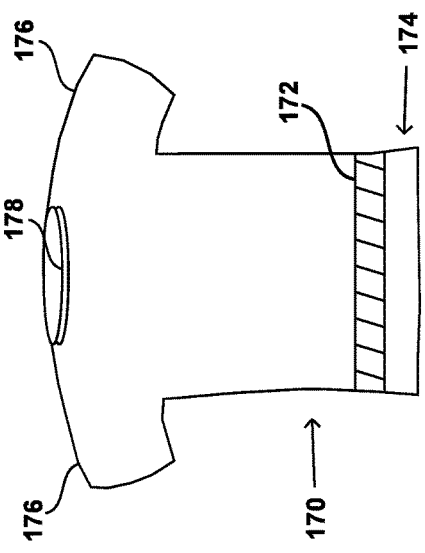
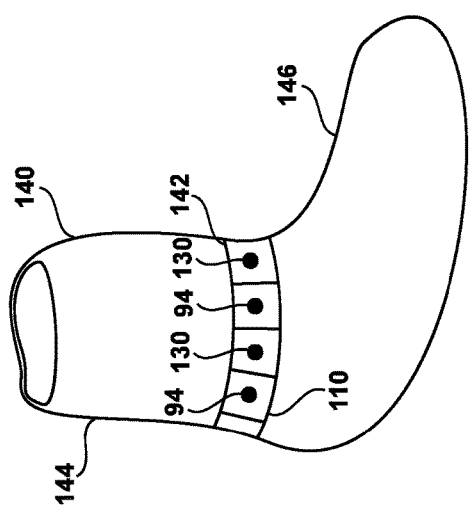
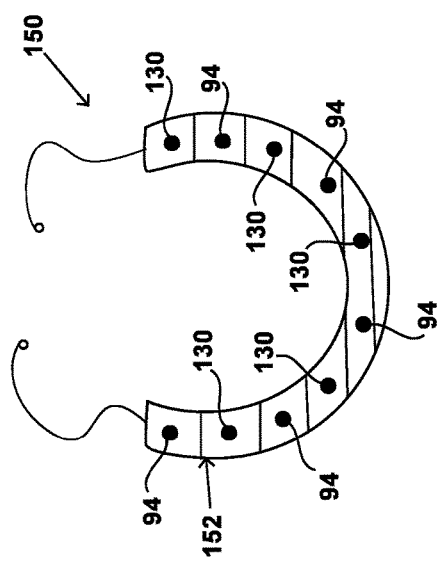

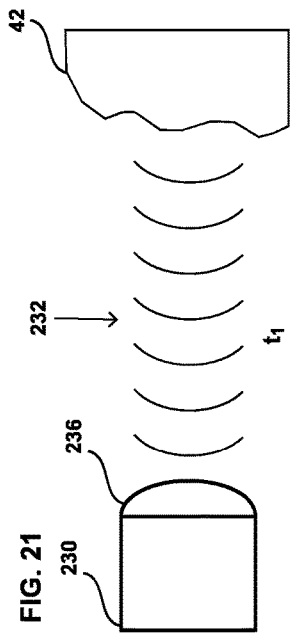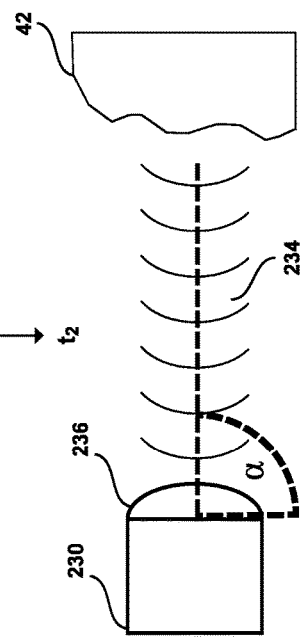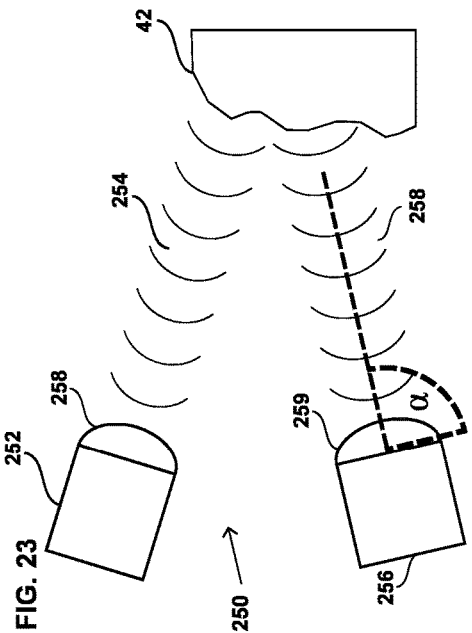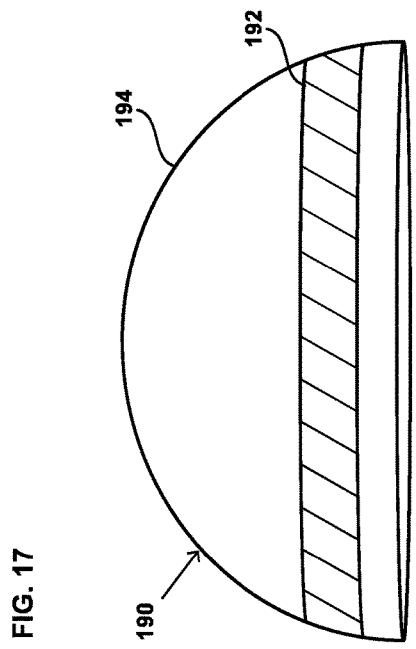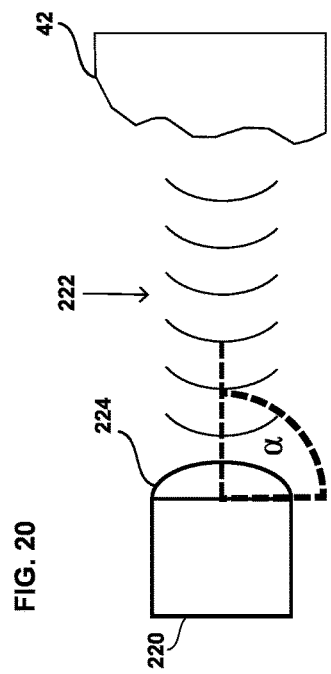

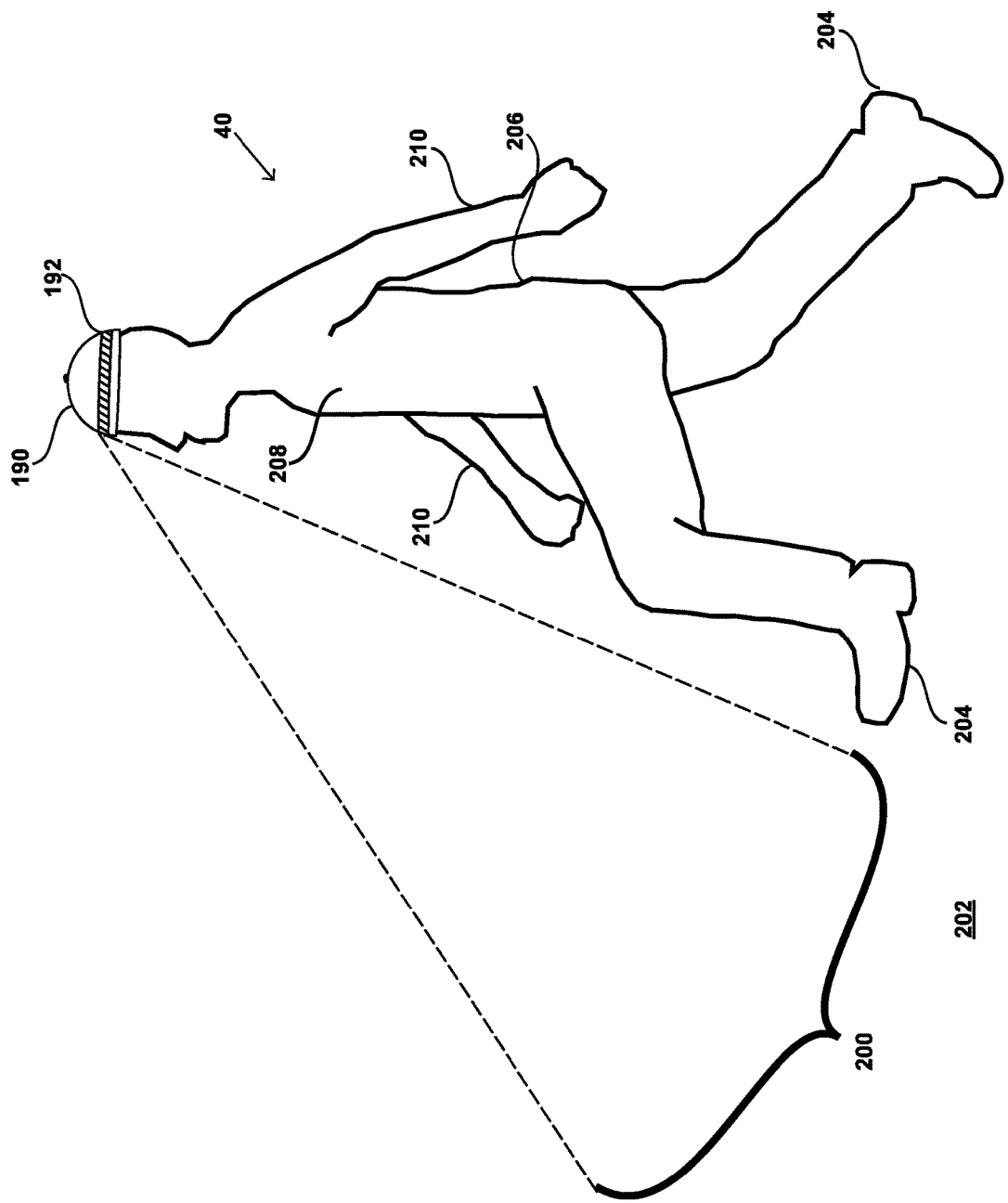

ITEM ATTACHABLE TO A SUBJECT AND INCLUDING A SENSOR FOR SENSING AN OBJECT THAT A BODY PORTION OF THE SUBJECT MAY CONTACT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

RELATED APPLICATIONS

U.S. patent application Ser. No. 14/634,304, titled DEVICE THAT DETERMINES THAT A SUBJECT MAY CONTACT A SENSED OBJECT AND THAT WARNS OF THE POTENTIAL CONTACT, naming Roderick A. Hyde, Muriel Y. Ishikawa, Jordin T. Kare, Eric C. Leuthardt, Mark A. Malamud, Tony S. Pan, Elizabeth A. Sweeney, Clarence T. Tegreene, Charles Whitmer, Lowell L. Wood, Jr., and Victoria Y. H. Wood, as inventors, filed Feb. 27, 2015, is related to the present application.

U.S. patent application Ser. No. 14/634,321, titled DEVICE HAVING A SENSOR FOR SENSING AN OBJECT AND A COMMUNICATOR FOR COUPLING THE SENSOR TO A DETERMINER FOR DETERMINING WHETHER A SUBJECT MAY COLLIDE WITH THE OBJECT, naming Roderick A. Hyde, Muriel Y. Ishikawa, Jordin T. Kare, Eric C. Leuthardt, Mark A. Malamud, Tony S. Pan, Elizabeth A. Sweeney, Clarence T. Tegreene, Charles Whitmer, Lowell L. Wood, Jr., and Victoria Y. H. Wood, as inventors, filed Feb. 27, 2015, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

An embodiment of a device includes at least one sensor, a determiner, and a notifier. The at least one sensor is configured to be located on a body portion of a subject and to sense an object. The determiner is configured to determine, in response to the sensor, whether the body portion may contact the object. The notifier is configured to notify the subject in response to the determiner determining that the body portion may contact the object.

Such a device may be useful to sense an object that may make contact with a body part in which the subject has lost feeling or proprioception. For example, a subject who has Type I diabetes may lose feeling in, or proprioception of, one or both of his/her feet, and, as a result, may, while walking, unknowingly injure his/her toes to the point of bloodying them by unknowingly bumping his/her feet into objects (e.g., stairs, furniture, curbs, door jambs, toys). The above-described device, which may be worn on a foot, or which may be part of, a shoe, may prevent the diabetic from injuring his/her toes by warning him/her of a potential collision between his/her feet and an object in time for the subject to take corrective action. Furthermore, the item on which the sensor is disposed may be a piece of clothing (e.g., shoe, sock) or jewelry (e.g., anklet) that allows a subject to "wear" the sensor inconspicuously. Other applications of the above-described device are contemplated. For example, the device may prevent a subject who is blind (permanently or temporarily due to, e.g., surgery), or who is in the dark, from walking into an object, and may prevent a subject who is walking in murky water from striking with his/her foot or shin, or stepping on, an underwater object. In addition, the device may help a subject, for example one who is unsteady on his/her feet, who has limited neck or head mobility (e.g., because he/she is recovering from surgery such as heart or back surgery), or who has permanent spinal damage, from tripping on an object while relieving the subject of the need to look down to watch where his/her feet are.

BRIEF DESCRIPTION OF THE FIGURES

FIG. 12 is a side view of a system that includes a sock and a device of one or more of FIGS. 2 and 7-10, according to an embodiment.

FIG. 13 is a view of a system that includes a piece of jewelry and a device of one or more of FIGS. 2 and 7-10, according to an embodiment.

FIG. 14 is a view of a system that includes a pair of pants and a device of one or more of FIGS. 2 and 7-10, according to an embodiment.

FIG. 15 is a view of a system that includes a shirt and a device of one or more of FIGS. 2 and 7-10, according to an embodiment.

FIG. 17 is a view of a hat that includes a device of one or more of FIGS. 2 and 7-10, according to an embodiment.

FIG. 18 is a diagram of a human subject wearing the hat of FIG. 17, according to an embodiment.

FIG. 20 is a diagram of a passive sensor sensing an object, according to an embodiment.

FIG. 21 is a diagram of an active sensor transmitting a signal at one time, and sensing a portion of the signal redirected by an object at a later time, according to an embodiment.

FIG. 23 is a diagram of an active sensor simultaneously transmitting a signal and sensing a portion of the signal redirected by an object, according to another embodiment.

DETAILED DESCRIPTION

Figure 1:
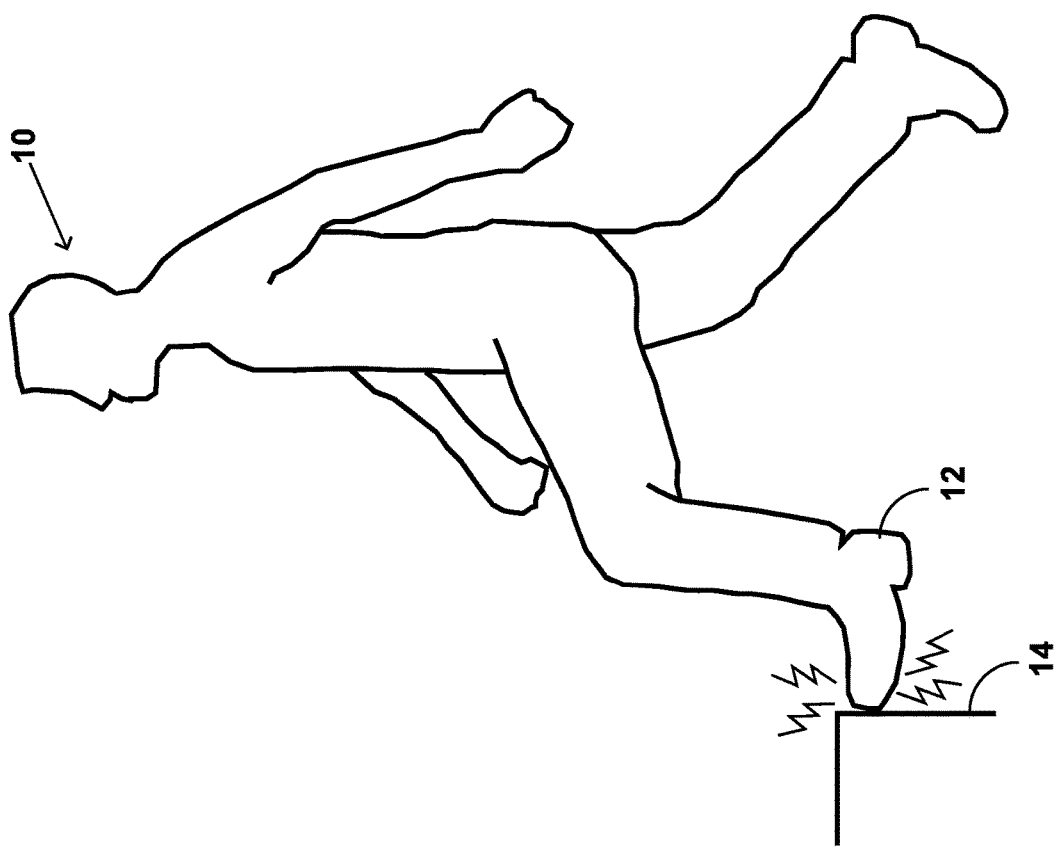
FIG. 1 is a diagram of a human subject striking his/her foot against an object while walking.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more embodiments are described with reference to the drawings, wherein like reference numerals may be used to refer to like elements throughout. In the following description, for purposes of explanation, numerous specific details are set forth in order to provide a thorough understanding of the one or more embodiments. It may be evident, however, that one or more embodiments may be practiced without these specific details. In other instances, well-known structures and devices are shown in block-diagram form in order to facilitate describing one or more embodiments.

Diseases, injuries, and other afflictions may cause a subject to lose the ability to feel a portion of his/her body, to lose the ability to feel pain in the body portion, to lose proprioception for the body portion, or to lose two or more of the ability to feel, the ability to feel pain in, and proprioception for, the body portion. Proprioception is the ability of a subject to know a relative position and location of a body portion even without being able to see the body portion or to touch the body portion to a known point of reference; for example, a subject typically has a sense of where his/her foot is even if he/she is not looking at the foot and is not contacting the ground with the foot. Type I diabetes is an example of a disease that can cause loss of feeling in, the inability to feel pain in, and proprioception regarding, a body portion by damaging nerves in and to the body portion.

Referring to FIG. 1, a consequence of such a loss of the ability to feel, of the ability to feel pain in, or of proprioception for, a body portion is that a subject 10 may inadvertently and repeatedly injure the body portion without being aware that the body portion is injured, at least until well after the activity (e.g., walking) that caused the injury. For example, if the subject 10 has Type I diabetes, then he/she may have lost the ability to feel pain in, and proprioception regarding, his/her foot 12. As a consequence, he/she may inadvertently strike, with his/her foot 12, an object 14 such as a stair, door jamb, curb, piece of furniture, toy, or debris, without realizing that the contact with the object has injured his/her foot. That is, even though the subject 10 may sense the contact between his/her foot 12 and the object 14 (e.g., by experiencing a stumble while walking), the lack of functioning pain receptors in the foot may lull the subject into believing that no injury resulted from the contact; and, the loss of proprioception may exacerbate the injury to the foot by increasing the frequency of such strikes to a level that does not allow for complete healing of an injury caused by a prior strike before the next strike occurs.

Unfortunately, the cumulative effect of such inadvertent injuries to a body portion may be quite serious. For example, doctors have reported seeing Type I diabetics with foot injuries ranging from bloodied and bruised toes to gangrenous toes that require amputation.

Figure 2:
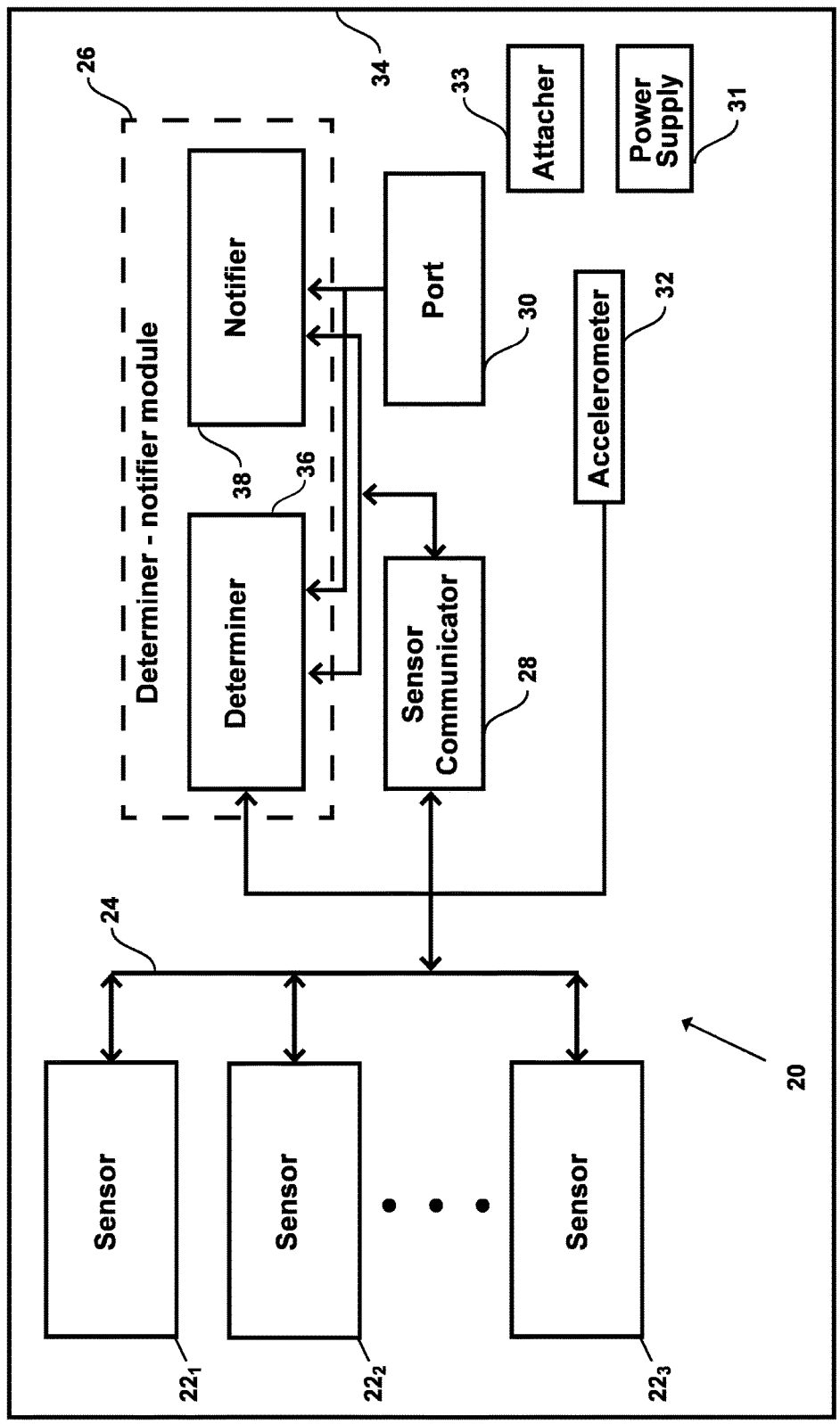
FIG. 2 is a diagram of a device, according to an embodiment

FIG. 2 is a diagram of an embodiment of a device 20, which is configured to sense an object that a body portion of a subject may contact, and to notify the subject, or a person with the subject, of the potential for contact in time for the subject to avoid such contact, or the person to aid in avoidance. For example, the device 20 may be attached to, or may be part of, a shoe, and may be configured to sense an object that a foot of a subject may contact, and to notify the subject, or a person with the subject, of the potential contact.

The device 20 includes one or more sensors $22_1$-$22_n$, a sensor bus 24, a determiner-notifier module 26, a sensor communicator 28, a communications port 30, a power supply 31, an accelerometer 32, an attacher 33, and a housing 34.

Each sensor 22 may be any type of sensor that is suitable for sensing an object with which a body portion (e.g., a foot) of a subject may collide. Examples of types of sensors suitable for use as a sensor 22 include ultrasonic, infrared, acoustic, Doppler, optics such as an image-capture device, radar, and scanning sensor. The sensor 22 may include a combination of more than one type of sensor. Furthermore, an accelerometer, separate from the accelerometer 32, is a type of sensor suitable for use as a sensor 22. Each sensor may have a sensing range (e.g., 0-5 meters) and a sense angle (e.g., 0-360°) suitable for an application of the device 20. In addition, the sensors 22 may be arranged to form one or more arrays of sensors. The sensors 22 are further described below in conjunction with FIGS. 18-23.

The sensors 22 may be spatially arranged on, e.g., a body portion of a subject or on an item that is attached to the body portion, in any manner that is suitable for sensing an object with which a body portion of a subject may collide. For example, the sensors 22 may be oriented in a same direction, or may be oriented in different directions to increase an overall sensing angle. The spatial arrangement of the sensors 22 is further described below in conjunction with FIGS. 12-17.

The sensor bus 24 is configured to allow two-way communication between the one or more sensors 22 and the sensor communicator 28 and to provide power to the one or more sensors from the power supply 31. The sensor bus 24 may be any suitable type of parallel or serial bus, such types including PCI, LPC, ISA, EISA, I²C, PCI Express, ATA, and SATA.

The determiner-notifier module 26 includes a determiner 36 and a notifier 38, which may be integral with one another, separate and attached to one another, separate and unattached to one another but in a same location, or separate and unattached to one another and in separate locations. Consequently, at least regarding the latter embodiment, the determiner-notifier module 26 may lack a housing or other item (e.g., an integrated-circuit die, a printed circuit board) in or on which both the determiner 36 and notifier 38 are disposed.

The determiner 36 is configured to determine whether a body portion of a subject may strike, collide with, or otherwise contact an object detected by one or more of the sensors 22. The determiner 36 is configured to make this determination in response to a signal, data, or other information that the one or more sensors 22 generate and provide to the detector 26 via the sensor communicator 28, and within a time frame that allows enough time for the subject to avoid the contact by, e.g., taking corrective action. The determiner 36 may be, or may include, one or more of an application-specific integrated circuit (ASIC), field-programmable gate array (FPGA), or an instruction-executing computing circuit such as a microcontroller or a microprocessor.

The notifier 38 is configured to generate a warning or other notification in response to the determiner 36 determining that a body portion of the subject may contact an object, and to so generate the notification within a time frame that allows enough time for the subject, or another person, to avoid the contact by, e.g., taking corrective action. The notifier 38 may be, or may include, one or more of an application-specific integrated circuit (ASIC), field-programmable gate array (FPGA), and an instruction-executing computing circuit such as a microcontroller or a microprocessor; for example, the determiner 36 and notifier may be disposed on a same ASIC, FPGA, or computing circuit. Furthermore, the notifier 38 may include stimulators that are configured to stimulate one or more senses (e.g., touch, sight, sound) of a subject (not shown in FIG. 2). For example, the notifier may include one or more vibrating elements that may be disposed on the body portion as on one or more shoes or that a subject may carry separately, such as in one or more of his pockets or as jewelry (e.g., a ring); an auditory stimulator that may be disposed on the body portion as in one or more shoe or anklet, or that a subject may carry separately such as wireless earbuds; or one or more visual stimulators such as light-emitting diodes (LEDs) disposed on one or more shoes.

The sensor communicator 28 is configured to provide one-way (sensor-to-determiner-notifier-module) or two-way communications between the one or more sensors 22 and the determiner-notifier module 26 via the bus 24.

The communications port 30 is configured to provide one-way (other-device-to-device 20) or two-way communications between the device 20 and another device (not shown in FIG. 2) such as a computing device. For example, the port 30 may allow one to program, or otherwise configure, the device 20 from a computing device such as a smart phone, and may allow uploading data from the one or more sensors 22 and the determiner-notifier module to the computing device. The port 30 may be any suitable type of port, such as Universal Serial Bus (USB), and may be wireless or connector-based.

The power supply 31 is configured to power the one or more sensors 22, the determiner-notifier module 26, the communicator 28, the port 30, the accelerometer 32, the attacher 33 (if the attacher consumes power), and other components of the device 20. The power supply 31 may be of any suitable type. For example, the power supply 31 may include a battery (not shown in FIG. 2), such as a microbattery or thin-film battery, that is rechargeable via the port 30. Or, the power supply 31 may generate power by converting light (e.g., with a solar cell, such as an ultrathin solar cell as described in U.S. Patent Pub. 20140216524, titled Arrays Of Ultrathin Silicon Solar Microcells, which is incorporated by reference), kinetic energy such as movement of the subject (e.g. using a kinetic-energy harvester), or a temperature differential between the subject and the ambient environment, into an electrical voltage or current, and may use this voltage or current to power the device 20, to recharge the battery, or to both power the device and recharge the battery. If the device 20 is implantable, then the power supply 31 may be configured to recharge a battery in response to electromagnetic waves that propagate from a source outside of the subject, through the subject's tissue (e.g., skin), and to the power supply or an antenna coupled thereto. The power supply 31 may further include circuitry to generate, from an input voltage (e.g., a battery voltage), a respective regulated voltage or current for each component of the device 20. Where the power supply 31 includes a battery, the power supply may generate, or cause the notifier 38 to generate, a notification when the charge stored on, or the voltage across, the battery falls below a threshold value. For example, if the battery charge is monitored, then the threshold value may be within a range of about 5%-50% of the full-charge level; or, if the battery voltage is monitored, then the threshold value may be within a range of about 80%-99% of the full-voltage level.

The accelerometer 32 is configured to provide information representative of a movement of the device 20, and, therefore, of a movement of the subject and the subject's body portion to which the sensor system is secured. For example, the accelerometer 32 may be a microelectromechanical (MEMs) device.

The attacher 33 is configured to attach, or to otherwise secure, the sensor system 20 to the subject, for example to the body portion of the subject, or to an item that is attached or otherwise secured to the subject, for example to the body portion of the subject. Examples of the attacher 33 include Velcro®, magnet, pin, clip, or adhesive for securing the device 20 to the subject or to an article of clothing worn by a subject. If the device 20 is implantable or is embedded within an item such as a shoe or another article of clothing, then the attacher 33 may be omitted.

The one or more sensors 22, bus 24, determiner-notifier module 26, communicator 28, port 30, power supply 31, accelerometer 32, and attacher 33, as well as any other components of the device 20, may be disposed within or on, or may be otherwise attached to, the housing 34, which may be configured for attachment to a subject, for example to the body portion of the subject. For example, the attacher 33 may be attached to the outside of the housing 34, and may attach the housing to the subject, for example to the body portion of the subject, or to an item (e.g., a shoe) worn or carried by the subject, for example on the body portion (e.g., a foot) of the subject; or the housing may be implantable, or may be embeddable within an item such as a shoe or another article of clothing, in which case the attacher may be omitted. Furthermore, the housing 34 may be a partial or full enclosure made from, for example, a suitable type of metal or plastic, or may be a platform, such as a rigid, conformable, flexible, or stretchable circuit board to which one or more other components of the device 20 are mounted, thereby forming together a stretchable electronic or flexible electronic device. The circuitry may include a serpentine design. Examples of conformable, flexible, or stretchable electronics are described in U.S. Patent Pub. 20100002402, titled Stretchable and Foldable Electronic Devices, and by Kim and Rogers in Adv. Mater. 2008, 20, 4887-4892, *Stretchable Electronics: Materials Strategies and Devices*, which publications are incorporated by reference.

Figure 3:
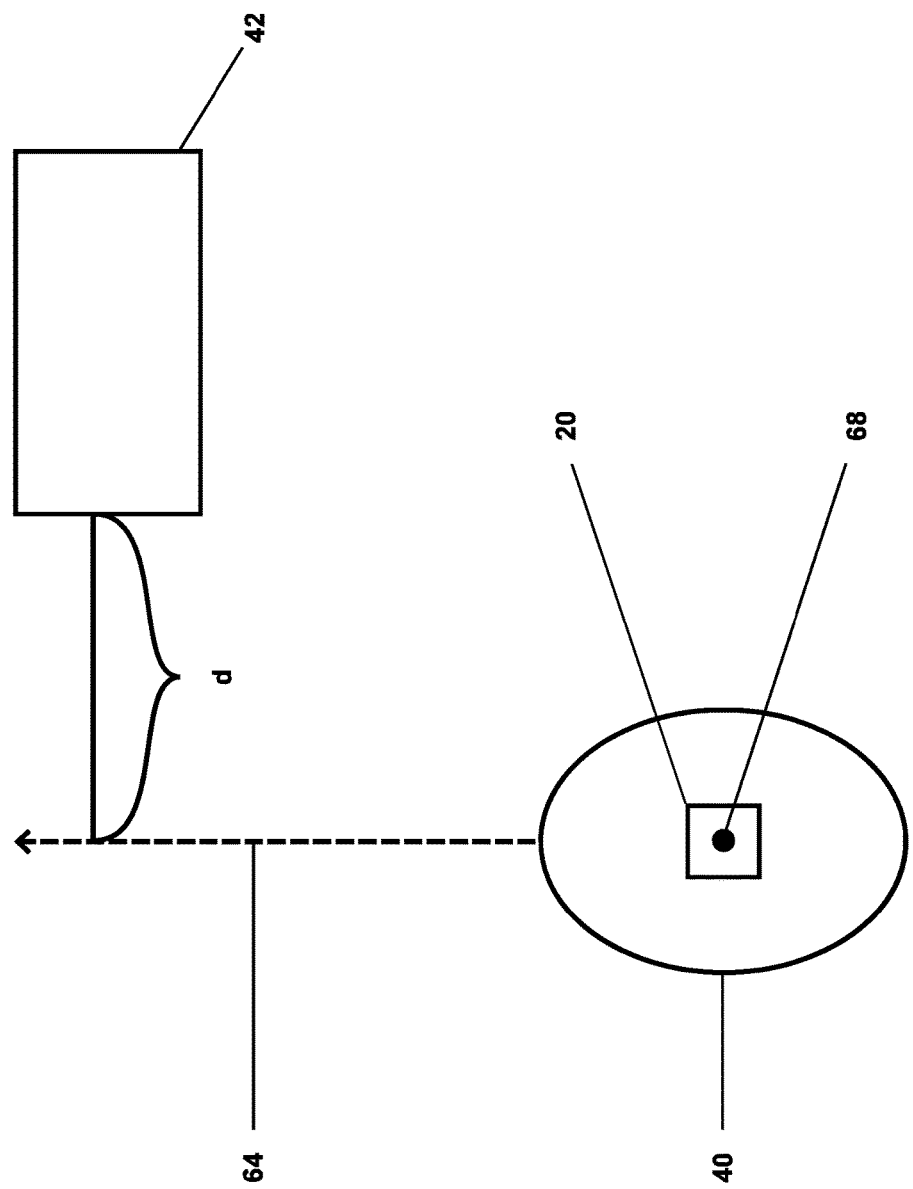
FIG. 3 is a diagram of a subject carrying the device of FIG. 2 and moving relative to a stationary object, according to an embodiment.

FIG. 3 is a diagram of a moving subject 40, a stationary detected object 42, and a device 20 of FIG. 2 attached to, or otherwise carried by, the subject, according to an embodiment. For example, the device 20 may be disposed on a shoe that the subject 40 wears on his foot, and the device may operate to warn the subject of a potential collision between his/her foot and the object 42.

Figure 4:
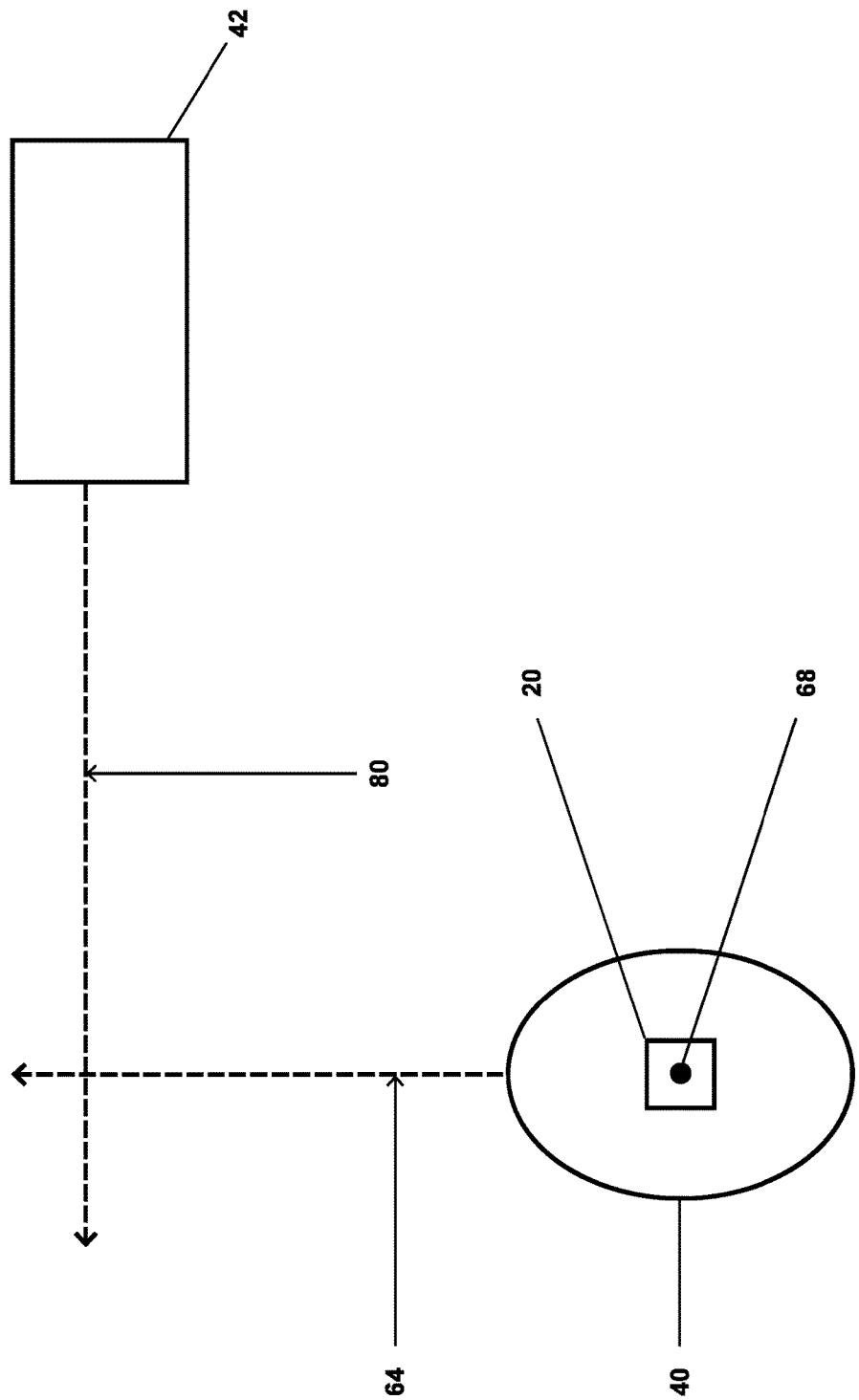
FIG. 4 is a diagram of a subject carrying the device of FIG. 2 and moving relative to a moving object, according to an embodiment.

FIG. 4 is a diagram of a moving subject 40, a moving detected object 42, and a device 20 of FIG. 2 attached to, or otherwise carried by, the subject, according to an embodiment. For example, the device 20 may be disposed on a shoe that the subject 40 wears on his foot, and the device may operate to warn the subject of a potential collision between his/her foot and the object 42.

Figure 5:
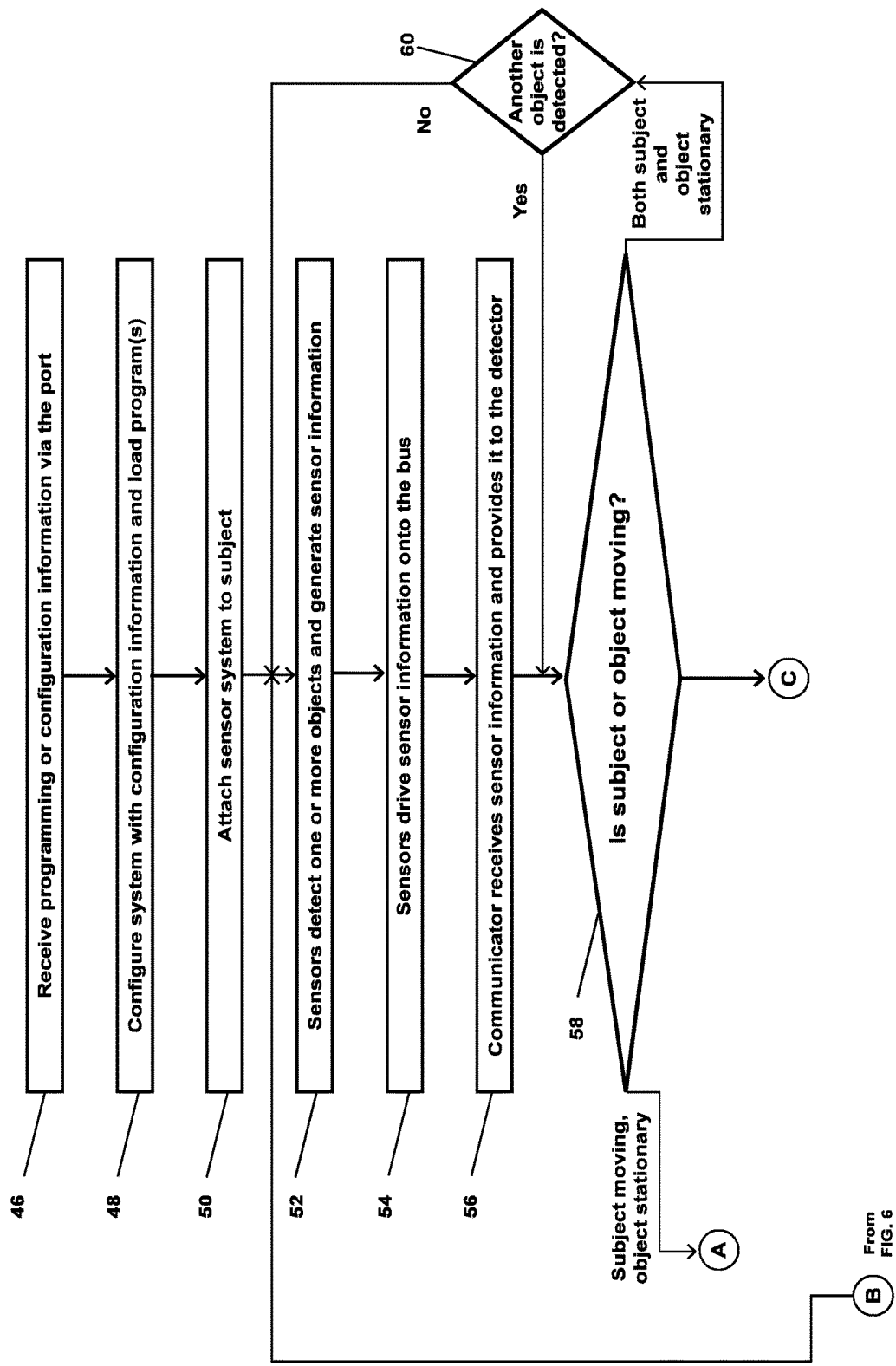
FIGS. 5 and 6 are a flow diagram of the operation of the device of FIG. 2, according to an embodiment.
Figure 6:
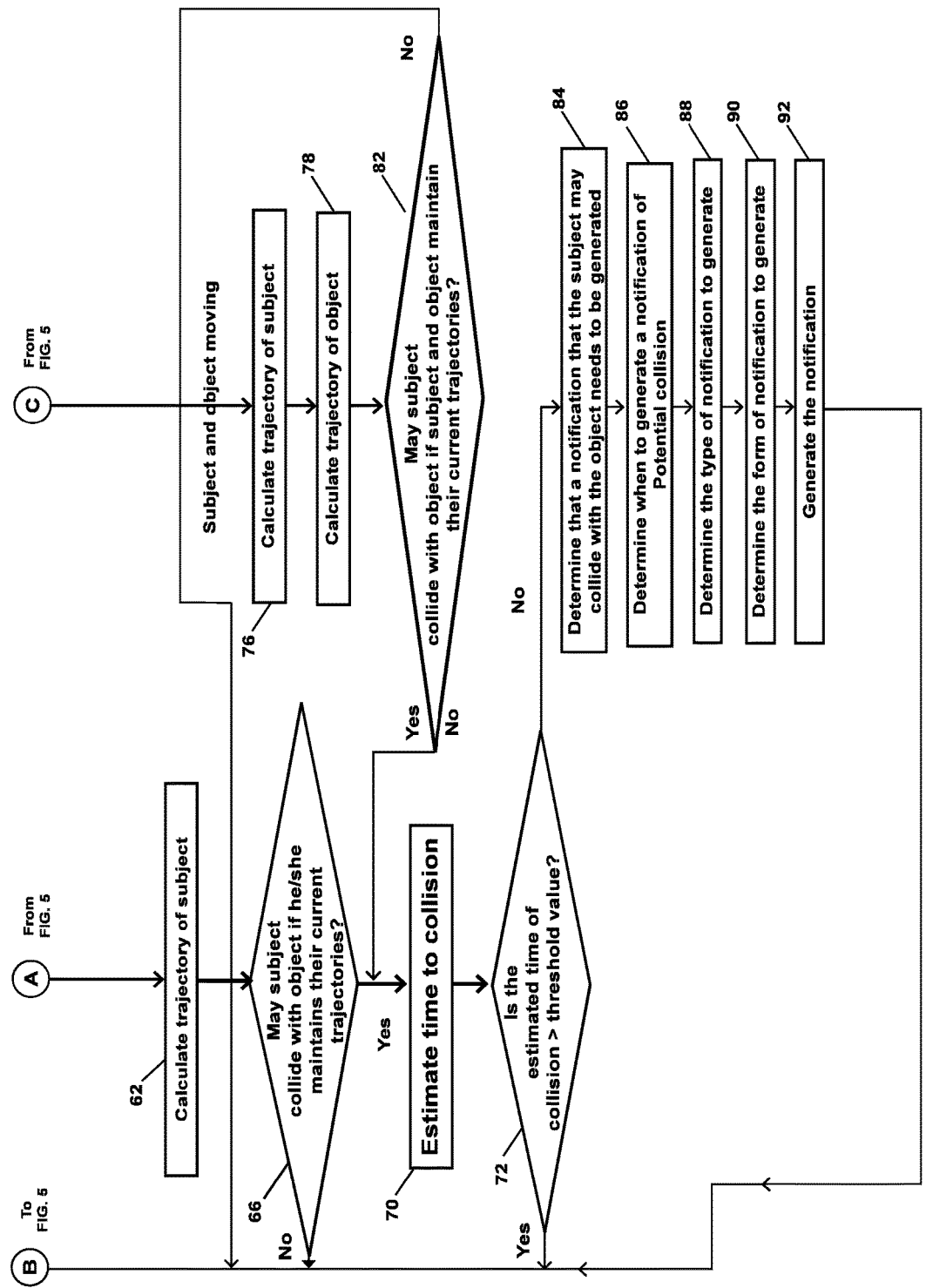

FIGS. 5 and 6 are a flow diagram of the operation of the device 20, according to an embodiment.

Referring to FIGS. 2-6, operation of the device 20 is described according to an embodiment.

At an optional step 46, the port 30 receives programming (e.g., software) or configuration (e.g., firmware) information from an external source (not shown in FIGS. 2-6) such as a computer or smart phone. Alternatively, the device 20 may have already been programmed or configured, e.g., by the manufacturer.

Next, at a step 48, the device 20 programs itself in response to the programming information, and configures itself in response to the configuration information. For example, the device 20 may configure operational characteristics (e.g., sensitivity, power, transmit-beam size, receive-lobe size) of the one or more sensors 22, including enabling only a selected one or more of the sensors, and may do so via the communicator 28. Or, the device 20 may configure the circuits (e.g., filter coefficients) to be used by the determiner 36 and the notifier 38, or may load a program to be executed by a computing circuit (e.g., a microprocessor or microcontroller) that implements portions of one or both of the determiner and the notifier.

Then, at a step 50, the subject 40, or another person (not shown in FIGS. 2-6) attaches the device 20 to the subject, for example to the body portion that may collide with the object 42, using the attacher 33, or otherwise places the system for carrying by the subject. For example, the device 20 may be embedded in, or otherwise attached to, an article of clothing, for example a shoe, or jewelry (e.g., an anklet) that the subject 40 puts on. Alternatively, at least the determiner 36 or notifier 38 may be disposed on another device such as a personal computing device (e.g., a smart phone).

Next, at a step 52, if one or more of the sensors 22 are active sensors, then the enabled one or more of these active sensors each scans a respective region for objects 42 within the range of the enabled one or more sensors. For example, the enabled one or more of the sensors 22 may scan for, and have the ability to detect, objects (e.g., stairs, furniture, door jambs, baseboards, curbs, toys, or debris) 42 that the subject 40 may inadvertently "bang into" with his/her foot and that are within, e.g., 0-5 m of the sensor. As a further example, the enabled sensors 22 may be configured to act as an array of sensors, and the determiner 36 may be configured to process information from the one or more enabled sensors in a manner suitable for the one or more sensors configured as an array of sensors. Active sensors are described below in conjunction with FIGS. 19-22.

Still at step 52, alternatively, if one or more of the sensors 22 are passive sensors, then the enabled one or more of these passive sensors each "listens" for objects 42 within the range (e.g., 0-5 m) of the sensor. For example, the enabled sensors 22 may be configured to act as an array of sensors, and the determiner 36 may be configured to process information from the one or more enabled sensors in a manner suitable for the one or more sensors configured as an array of sensors. Passive sensors are further described below in conjunction with FIGS. 17 and 23.

Then, still at step 52, each of the enabled sensors 22 that detects an object 42 generates a sensor signal, sensor data, or other sensor information related to the detected object (if a sensor detects more than one object, then it may generate respective sensor information related to each of the detected objects). For example, such sensor information may include one or more of a range, azimuth, elevation, size, type (e.g., soft, hard, moveable, immoveable), position, velocity, and acceleration of the object, or may be sufficient for the determiner 36 to determine one or more of these parameters. The parameters such as range, azimuth, elevation, position, velocity, and acceleration of a detected object 42 may be relative to the device 20, to the sensor 22 generating the sensor information, to the subject 40, or to a body portion (e.g., a foot) of the subject (e.g., a body portion to which the sensor system is attached).

Next, at a step 54, each of the enabled sensors 22 that detect an object 42 drives this sensor information onto the bus 24. For example, the information may be sent as one or more messages that each includes header information sufficient for the determiner 36 to determine which message comes from which sensor, which detected object 42 is associated with which sensor information (if the enabled sensors 22 detect multiple objects), and at what time the information or message was generated.

Then, at a step 56, the communicator 28 receives the sensor information from the bus 24 and provides it to the determiner 36. For example, the communicator 28 may strip headers from the information messages and provide the information to respective locations (e.g., memory buffers) of the determiner 36 as indicated by the headers.

Next, starting at a step 58, the determiner 36 analyzes the sensor information from the communicator 28 and information from the accelerometer 32 to determine if a body portion of the subject 40 may collide with, or otherwise contact, a detected one of the objects.

First, at the step 58, the determiner 36 determines whether the subject 40 and a first one of the detected objects 42 are moving. The determiner 36 determines whether the subject 40 is moving in response to information generated by the accelerometer 34, and determines whether the object is moving in response to the sensor information from sensor 22 corresponding to the object. For example, the device 20 may include, as one or more of the sensors 22, a Doppler sensor for determining whether the object 42 is moving.

If, at step 60, the determiner 36 determines that neither the subject 40 nor the first one of the detected objects 42 is moving, then the determiner determines that the subject and object will not collide with each other if they maintain their present states (not moving), and returns to step 58 to determine whether the next detected object (if more than one object is detected) is moving. If no other objects 42 are detected, then the determiner 36 returns to step 52 and awaits the detection of another object.

Referring to FIGS. 2-3 and 5, if the determiner 36 determines that the subject 40 is moving but that the first one of the detected objects 42 is stationary, then the determiner proceeds as follows:

At a step 62, the determiner 36 calculates, in response to the information generated by the accelerometer 32, a trajectory 64 of the subject 40, where the trajectory includes one or more of the acceleration, velocity, and relative position of the subject—even though the accelerometer may generate only information representative of the acceleration of the subject, because velocity is the integral of acceleration and position is the integral of velocity, the determiner 36 may calculate at least the velocity and the relative position of the subject from the accelerometer information. As an example, the accelerometer 32 may detect each step that the subject 40 takes, and from this step detection the determiner 36 may determine the subject's stride rate. And from the subject's stride length, the determiner 36 may determine the velocity equal to the product of the stride rate and the stride length. Because the stride length of the subject 40 may change with stride rate (e.g., stride length increases the faster the subject walks or runs), the stride lengths of the subject 40 at different stride rates may have been determined previously and stored in a look-up table (not shown in FIG. 2) such that for a calculated stride rate, the determiner 36 may look up the corresponding stride length. Alternatively, the device may include a positioning sensor (not shown in FIG. 2) configured to provide information from which the determiner 36 may calculate the trajectory 64 of the subject 40. Examples of such a positioning sensor include a global positioning sensor (GPS) or building positioning sensors using WiFi or Bluetooth beacons. Furthermore, although, for example purposes, the trajectory 64 is shown as being parallel to the ground in FIG. 3, it may have another direction that is not parallel to the ground.

Then, at a step 66, the determiner 36 determines whether the subject 40 may collide with the object 42 if the subject maintains his/her current trajectory 64. The determiner 36 may build in some tolerance for this calculation. For example, assume that the device 20 is located along a vertical line 68 (out of the page of FIG. 3) at the geometrical horizontal center of the subject 40, and a line representing the trajectory 64 emanates from the vertical line, and thus from the horizontal center of the subject. If the object 42 is ground based, then even if the device 20 is not headed for the object, i.e., the line representing the trajectory 64 does not intersect the object, one of the subject's feet (not shown in FIG. 3) might be headed for a collision with the object. Therefore, the determiner 36 may determine that if a normal distance d between the trajectory line and the object 42 is less than a threshold (e.g., approximately three feet), then the determiner determines that the subject 40 may collide with the object if the subject maintains his/her current trajectory 64.

If the determiner 36 determines that the subject 40 will not collide with the object 42 if the subject maintains his/her current trajectory 64, then the determiner 36 returns to step 52 and repeats the above procedure to monitor the trajectory of the subject 40 and the object 42, or repeats the above procedure for a next object.

If, however, the determiner 36 determines that the subject 40 may collide with the object 42 if the subject maintains his/her current trajectory 64, then, at a step 70, the determiner estimates the time to a collision with the object with the assumption that the subject maintains his/her current velocity and acceleration.

At a step 72, the determiner 36 determines whether the estimated time of collision is greater than a threshold value; an example range of the threshold value is between six and ten seconds.

If the estimated time of collision is greater than a threshold value, then the determiner 36 returns to step 52 and continues to monitor the trajectory 64 of the subject 40 until the estimated time of collision is equal to or is less than the threshold value, or until the determiner determines that the trajectory of the subject has changed enough so that there will be no collision. The purpose of this delay is to prevent the determiner 36 from giving a false indication of a collision to the notifier 38, i.e., while there is still a significant time before the estimated collision during which the subject 40 may stop or significantly change his/her trajectory 64.

If the estimated time of collision is equal to or is less than the threshold value, then, at a step 84, the determiner 36 determines that it will proceed to order the notifier 38 to generate a notification, and determines the estimated time of (or time to) the potential collision and the direction, relative to the subject, from which the subject is approaching the object. For example, the determiner 36 may determine that the stationary object 42 is to the left of, to the right of, or straight ahead of, the subject 40. If, however, the determiner 36 later determines that the collision will not occur, then the determiner may rescind any previous notification-generation order to the notifier 38. The operation of the notifier 38 is described further below.

Still referring to FIGS. 2-3 and 5, if the determiner 36 determines that the subject 40 is stationary but that the detected object 42 is moving, then the determiner proceeds in a manner similar to that described above for the subject-moving-but-object-stationary scenario, but with the moving object replacing the moving subject in the above-described procedure. That is, the determiner 36 determines the trajectory of the object 42 and whether the object may collide with the subject 40 if the object maintains its current trajectory; and if the determiner determines that the object may collide with the subject, then the determiner determines that it will proceed to order the notifier 38 to generate a notification, and estimates the time to (or the estimated time of) the potential collision, and the direction, relative to the subject, from which the moving object is approaching the stationary subject.

Referring to FIGS. 2, 4, and 5, if, at the step 58, the determiner 36 determines that both the subject 40 and the detected object 42 are moving, then the determiner proceeds as follows:

First, at a step 76, the determiner 36 calculates the current trajectory 64 of the subject 40, including one or more of the acceleration, velocity, and relative position of the subject, in response to the information generated by the accelerometer 32, as described above. Although the trajectory 64 is shown as being parallel to the ground in FIG. 4, it may have another direction that is not parallel to the ground.

Then, at a step 78, the determiner 36 calculates a current trajectory 80 of the moving object 42, including one or more of the acceleration, velocity, and relative position of the object, in response to the information generated by one or more of the enabled sensors 22. The determiner 36 may calculate the trajectory 80 of the object 42 in a direction that is not parallel to the ground, although, for example purposes, the object's trajectory is shown as being parallel to the ground in FIG. 4.

Next, at a step 82, the determiner 36 determines whether the subject 40 may collide with the object 42 if both the subject and the object maintain their current trajectories 64 and 80. The determiner 36 may build in some tolerance for this calculation in a manner similar to that described above in conjunction with FIGS. 2-3 and 5.

If, at step 82, the determiner 36 determines that the subject 40 will not collide with the object 42 if the subject and object maintain their current trajectories 64 and 80, then the determiner returns to step 52 and repeats the above procedure to monitor the trajectories of the subject and the object, or to repeat the above procedure for another detected object.

If, however, the determiner 36 determines that the subject 40 may collide with the object 42 if the subject and the object maintain their current trajectories 64 and 80, then, at the step 70, the determiner estimates the time of (or the time to) a collision of the subject with the object if the subject and object maintain their current trajectories.

If, at the step 72, the estimated time of collision is greater than a threshold value, then the determiner 36 returns to the step 52 and continues to monitor the trajectories 64 and 80 of the subject 40 and the object 42 until the estimated time of collision is equal to or is less than the threshold value, or until the determiner determines that at least one of the trajectories has changed enough so that there will be no collision. The purpose of this delay is to prevent the determiner 36 from giving a false indication of a collision to the notifier 38 as described above.

Still at the step 72, if, however, the estimated time of collision is equal to or less than the threshold value, then, at the step 84, the determiner 36 determines that it will proceed to order the notifier 38 to generate a notification, and determines the estimated time of (or time to) the potential collision and the direction, relative to the subject, from which the subject and the object are approaching one another. If, however, the determiner 36 later determines that a collision will not occur, then it may rescind any previous notification-generation order to the notifier 38.

Referring to FIGS. 2-6, in response to a notification order from the determiner 36, the notifier 38 provides a corresponding notification, or warning, to the subject 40, or to another person, such as a caretaker of the subject, as described below.

First, at a step 86, the determiner 36 determines when to generate the notification in response to the previously determined estimated time of collision. The determiner 36 is configured to cause the notifier 38 to generate the notification far enough in advance of the potential collision to allow the subject 40 the opportunity to avoid the collision, but not so far in advance that the notification confuses the subject or renders moot a rescind-notification order from the determiner 36. For example, the determiner 36 may cause the notifier 38 to generate the notification three to five seconds before the estimated time of the potential collision.

Next, at a step 88, the determiner 36 determines the type of notification for the notifier 38 to generate. Each type of notification recommends to the subject 40, or to another person, such as the subject's caretaker, an action to take to avoid, or lessen the severity of, a potential collision. Examples of the types of notification include "stop," "slow down," "shorten stride", "look down and proceed with caution," "veer left," "veer right," "stairs ahead," "curb ahead," "moving object ahead," "object to the left," and "object to the right."

Then, at a step 90, the determiner 36 determines the pattern of the notification. Examples of the pattern of notification include one more patterns of, e.g., continuous or intermittent stimulation. Furthermore, the notifier 38 of the device 20 determines the type of the notification. Examples of the type of notification include visual, audial, vibratory, haptic, and nerve stimulation. For example, the notifier 38 may include an array of light-emitting diodes (LEDs), and activating steadily one or more red LEDs according to a pattern provided by the determiner 36 may recommend stopping, flashing one or more red LEDs according to a pattern provided by the determiner may recommend proceeding with caution, two flashes of a white LED according to a pattern may recommend veering right, etc. In another example, a haptic sensation of two "taps" or vibrations emanating from a right side of the device 20, for example in a shoe, according to a pattern provided by the determiner 36 may recommend veering right, and a haptic sensation of two "taps" on a left side of the device, for example in a shoe, according to a pattern, may recommend veering left. In yet another example, a beeping sound emanating from the notifier 38 of the device 20, for example in a shoe or housed remotely, according to a pattern provided by the determiner 36, may indicate "proceed with caution." In still another example, the notifier 38 may be remote from the determiner 36, and the determiner may transmit, via the port 30, an order to the notifier to generate a notification, where the order includes the pattern of the notification. For example, the notifier 38 may be, or include, a wireless (e.g., Bluetooth®) headset (not shown in FIGS. 2-6) that the subject 40 is wearing and that is configured to generate audial notifications; or, the notifier 38 may be or include, a wireless (e.g., Bluetooth®) pair of glasses or visor (not shown in FIGS. 2-6) that the subject is wearing and that is configured to generate visual notifications.

Next, at a step 92, the notifier 38 generates the notification according to the pattern determined by the determiner 36 and the type determined by, or inherent to, the notifier.

Then, the determiner 36 returns to the step 52 and repeats the above procedure for one or more other sensed objects 42. If there are not more sensed objects, or the subject 40 (or another person) powers down the device 20, then the procedure ends.

Referring to FIGS. 2-6, alternate embodiments of the device 20 are contemplated. For example, one or more of the above-described functions may be performed serially or in parallel. Furthermore, although described as determining a trajectory 64 of the subject 40, the determiner 36 may determine a trajectory of a body portion, such as one or more feet, of the subject instead of, or in addition to, determining the trajectory of the subject. Moreover, although the subject 40 is described as carrying, or having attached, only one device 20, the subject may carry (or have attached) multiple devices (e.g., one device on each foot). In addition, the device 20 may detect and track multiple objects 42 simultaneously, and generate respective notifications for each object or group of objects. Furthermore, the above-described method may include additional or fewer steps, and the above-described steps may be performed in an order that is different from the order described. Moreover, if the determiner 36 determines that an object 42 is soft (e.g., pillow or grass) or otherwise unlikely to injure the subject 40 if the subject and object were to collide, then the determiner may not order the notifier 38 to generate a notification, of a potential collision with the object, and, therefore, may allow the collision to occur. In addition, although described as detecting and warning a subject of a potential collision between the subject and a body portion of the subject, the device 20 may be configured to notify the subject of an object even if the device determines that there is no, or little, chance of a such a collision. Furthermore, in addition to, or in place of, the accelerometer 32 (or one or more of the sensors 22), the device 20 may include a positioning sensor to determine a position of the subject 40. Examples of positioning sensors include a global-positioning-system (GPS) sensor, a sensor that works with an electronic building-positioning system or a landmark-based positioning system, or an environmental sensor. Moreover, in addition to, or in place of, the accelerometer 32 (or one or more of the sensors 22), the device 20 may include an image-capture sensor that allows comparison of reference images or registration fiduciaries to captured image, and the determiner 36 may determine a position of the subject from such a comparison.

Figure 7:
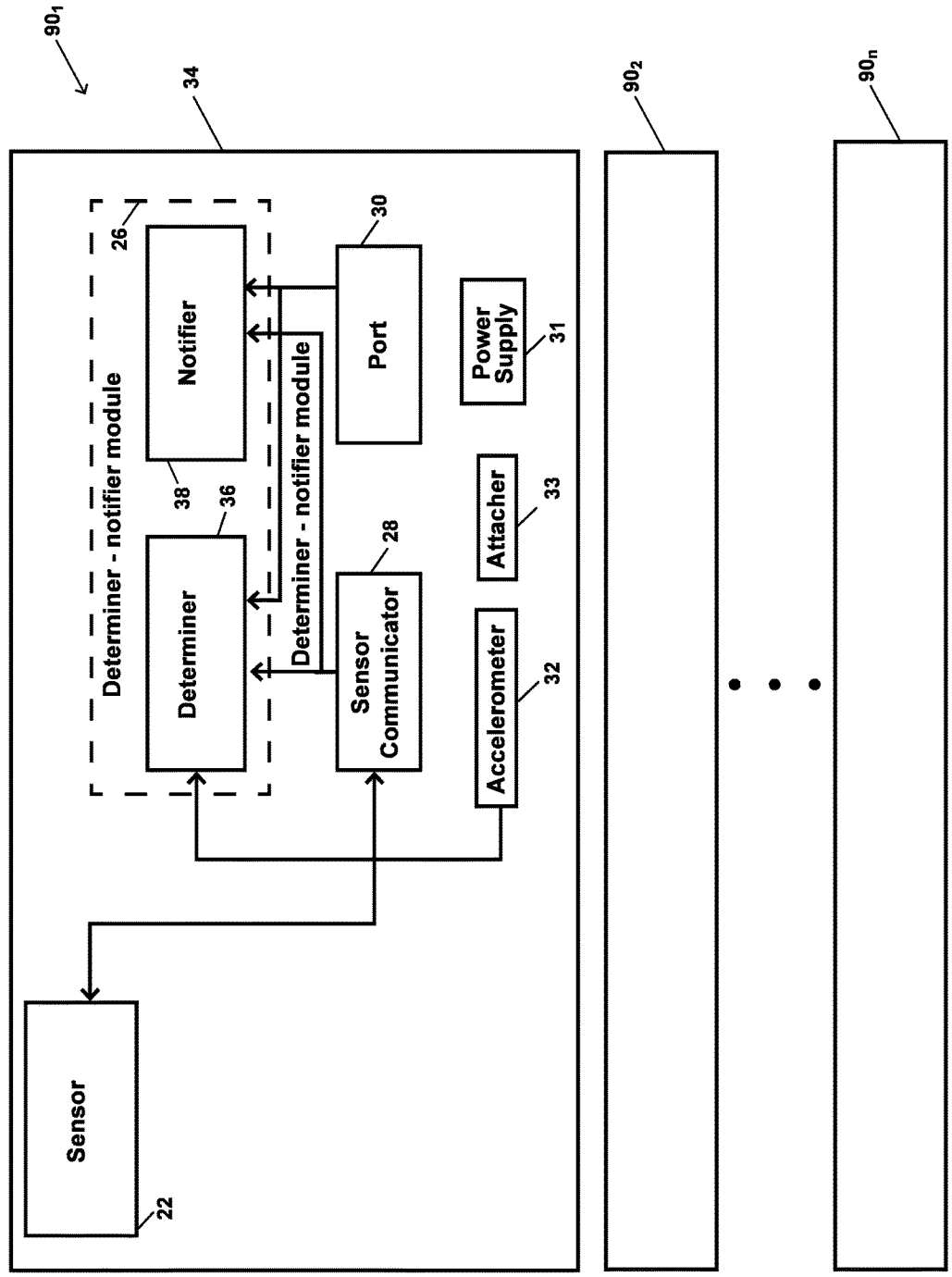
FIG. 7 is a diagram of a device, according to another embodiment.

FIG. 7 is a diagram of devices $90_1$-$90_n$, according to an embodiment. Each device 90 is similar to the device 20 of FIG. 2, but includes only a single sensor 22 paired with a respective determiner 36. Given today's integrated-circuit manufacturing processes, it may be easier or cheaper to make or use the devices 90 having single sensors than it is to make or use the device 20 having multiple sensors.

Consequently, to attach, or otherwise secure, multiple sensors 22 to a subject, one may attach, or otherwise secure, multiple devices 90 to the subject, e.g., to the body portion of the subject, or to an item that is worn, attached, or otherwise secured to the subject; for example, one may attach multiple devices 90 to a shoe worn by a subject to detect and warn of potential collisions of objects with the subject's feet.

Still referring to FIG. 7, alternate embodiments of the devices 90 are contemplated.

Figure 8:
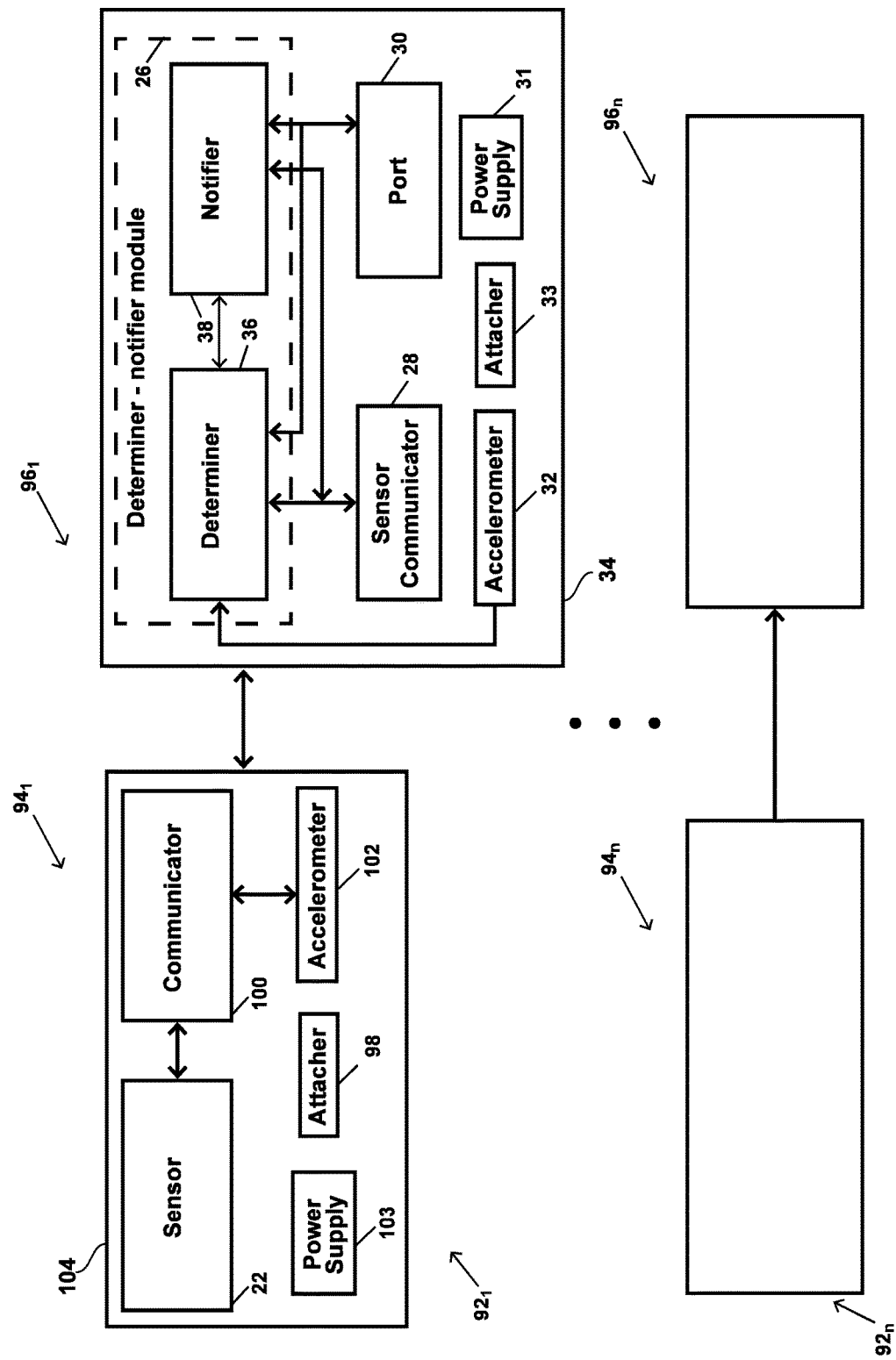
FIG. 8 is a diagram of a device, according to yet another embodiment.

FIG. 8 is a diagram of devices $92_1$-$92_n$, according to an embodiment. In this embodiment, the sensors 22 may be separated from the determiner-notifier module 26 so that each sensor may be disposed remotely from its corresponding determiner-notifier module.

Each device 92 includes a sensor module 94 and a base module 96, which communicate with each other wirelessly. The modules 94 and 96 may be attachable or otherwise securable to a subject, e.g., to a body portion of the subject. For example, the sensor modules 94 may be attachable to a shoe worn by a subject, and the base modules 96 may be locatable remotely from the sensor modules (e.g., in the subject's pocket); but together, the modules 94 and 96 cooperate to detect and warn the subject of potential collisions between objects and one or both of the subject's feet.

Each sensor module 94 includes a sensor 22, attacher 98, communicator 100, accelerometer 102, power supply 103, and a housing 104.

And each base module 96 includes a determiner-notifier module 26 including a determiner 36 and a notifier 38, a communicator 28, a port 30, a power supply 31, an accelerometer 32, an attacher 33, and a housing 34.

Each sensor module 94 may be attached or otherwise secured to a location of a subject that is remote from a location of the corresponding base module 96. For example, one or more sensor modules 94 may be located on a subject's foot (or on a shoe worn on the foot), and the corresponding detector modules may be located in one or more of the subject's pockets or on a separate item such as a ring. Or, the corresponding base modules 96 may be located remote from the subject (the accelerometers 102 allow the corresponding determiner-notifier modules 26 to determine the trajectory of the subject or of a body portion of the subject even though the modules 26 are remote from the subject), such as in the pocket or purse of a caretaker of the subject.

In operation, the communicator 28 may transmit, e.g., wirelessly, programming, configuration, or other information to the sensor module 94, and the communicator 100 may transmit, wirelessly, sensor and accelerometer information to the base module 96. The communicators 28 and 100 may generate message headers with a unique code so that the communicator 28 "knows" which messages are from the communicator 100 and vice-versa. Also, the messages between the sensor modules 94 and their respective base modules 96 may be time or code-divisional multiplexed to prevent interference. Furthermore, the communicator 100 may transmit, wirelessly, to the communicator 28 a status, or other information, regarding the power supply 103, such as if it is time to replace a battery on the sensor module 94.

In the above-described aspects and in other aspects, the operation of each sensor module 94 and its corresponding base module 96 may be similar to the operation of the device 20 as described above in conjunction with FIGS. 2-6.

Still referring to FIG. 8, alternate embodiments of the devices 92 are contemplated.

Figure 9:
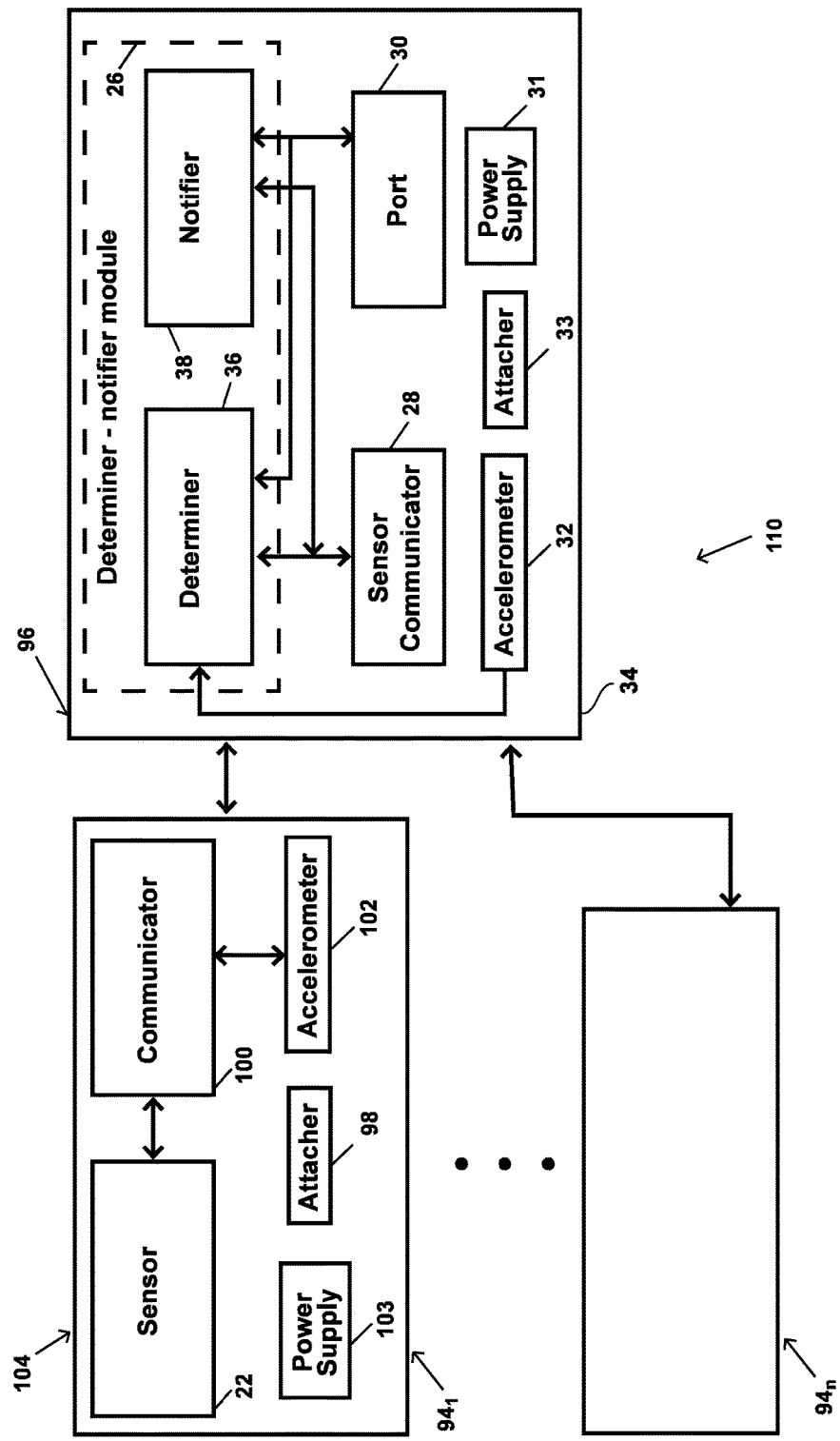
FIG. 9 is a diagram of a device, according to still another embodiment.

FIG. 9 is diagram of a device 110, according to an embodiment. The device 110 is similar to the set of devices $92_1$-$92_n$ of FIG. 8, except that the device 110 has only one base module 96. Allowing multiple sensor modules 94 to communicate with a same, single base module 96 may save costs, space, and complexity by not requiring a respective base module for each sensor module.

Still referring to FIG. 9, alternate embodiments of the device 110 are contemplated.

Figure 10:
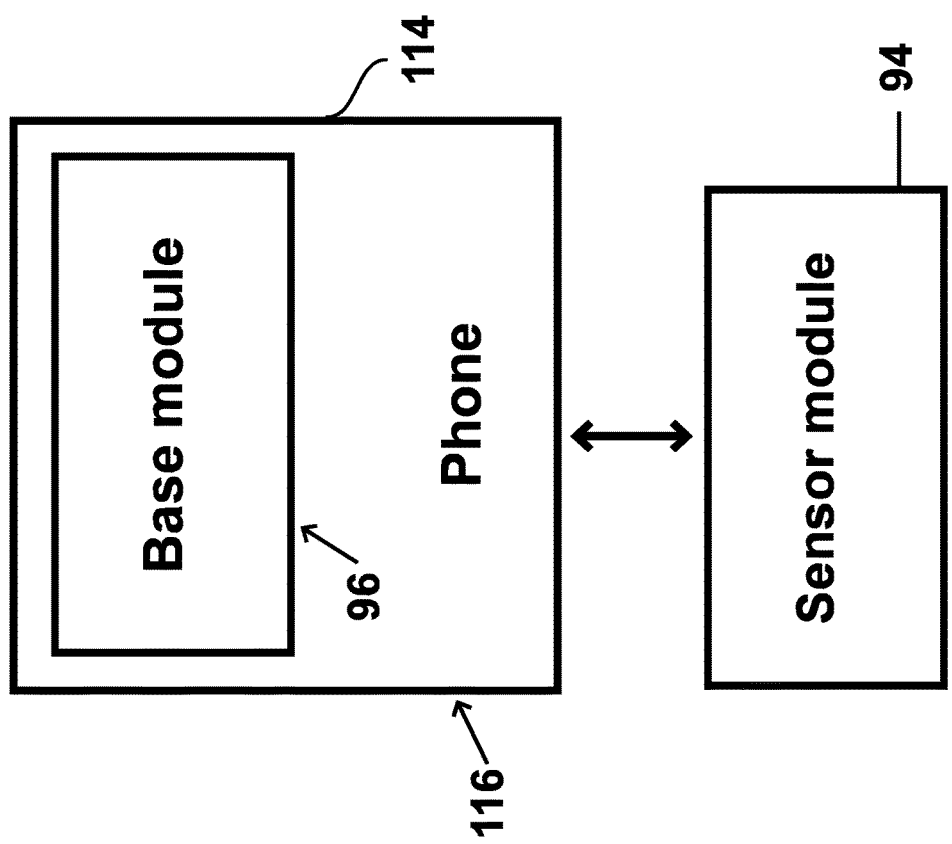
FIG. 10 is a diagram of a device, according to another embodiment.

FIG. 10 is a diagram of a device 116, according to an embodiment. In the device 116, one or more base modules 96 are disposed on a portable device 114 such as a smart phone or tablet computer, and one or more sensor modules 94 are disposed remotely from the portable device and communicate wirelessly with the one or more detector modules. For example, one may locate one or more of the sensor modules 94 on a subject's feet, and the subject, or a person with the subject, may carry the portable device 114 in a pocket or purse, or may wear the portable device on his/her person (e.g., a ring, watch, or other piece of jewelry).

Still referring to FIG. 10, alternate embodiments of the device 116 are contemplated.

Figure 11:
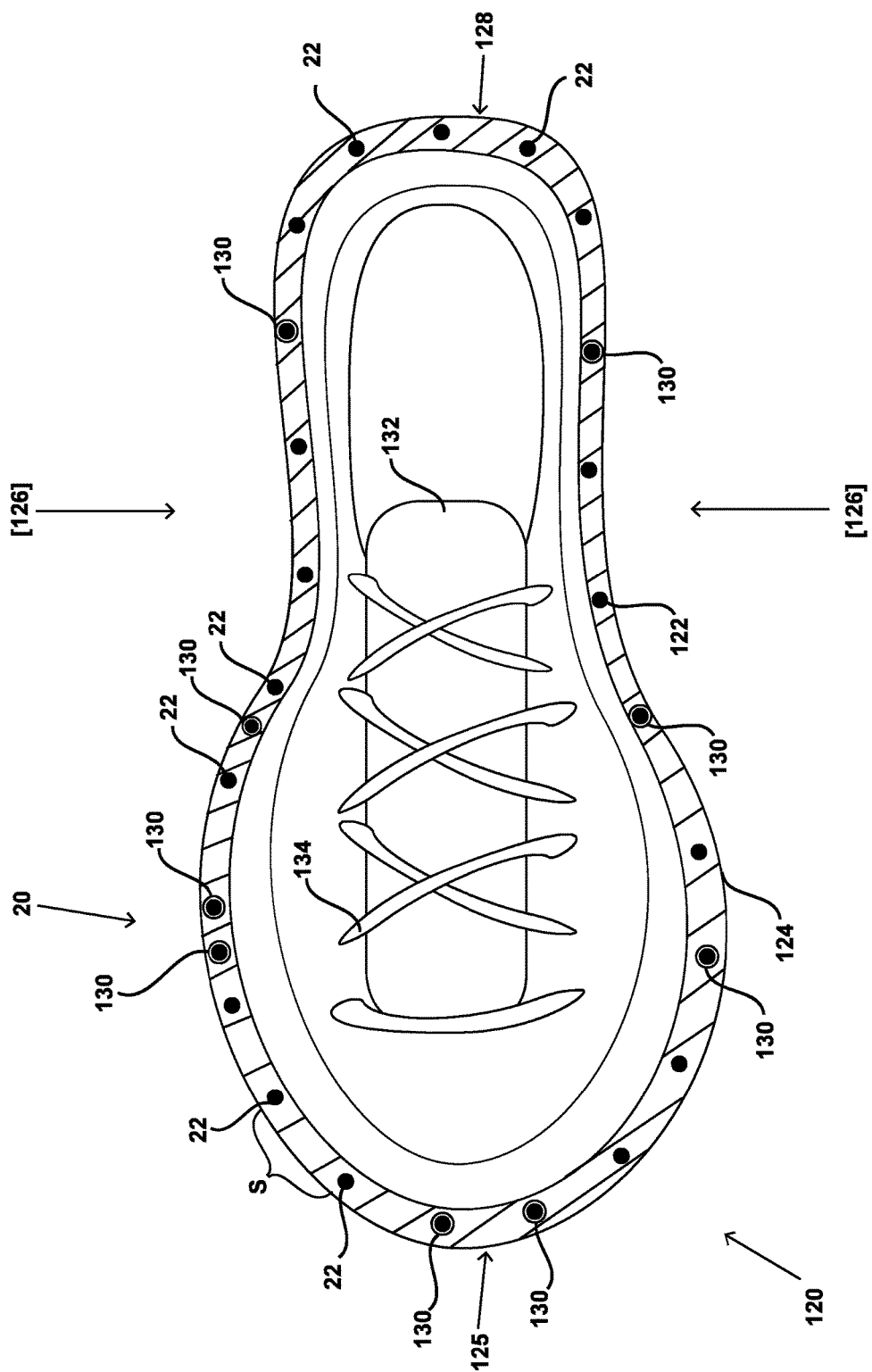
FIG. 11 is a plan view of a system that includes a shoe and at least one device of one or more of FIGS. 2 and 7-10, according to an embodiment.

FIG. 11 is a top plan view of a system, here a shoe 120, which includes a sensor assembly 122, according to an embodiment. The shoe 120 may detect a potential collision between a subject's foot and an object, and warn the subject, or a person with the subject, of the potential collision.

The sensor assembly 122 includes sensors 22 of FIG. 2, which may be arranged as, or act as, an array, and also includes other components (e.g., components of the determiner-notifier module 26) of the device 20 of FIG. 2 according to an embodiment.

The sensor assembly 122 is disposed around some, or all, of the periphery of the shoe 120 (the sensor assembly is shown as being disposed around the entire periphery in FIG. 11), and includes a substrate or platform 124, such as a flexible or stretchable printed circuit board, on which the sensors 22 of the device 20 (FIG. 2) are mounted. The sensor assembly 122 may be integral with, or stitched to, the shoe 120, or the sensor assembly may be attached to the shoe with adhesive (removable or non-removable) or Velcro® (removable); configuring the sensor assembly 122 to be removable may allow sharing of a single assembly among multiple shoes. Alternatively, the sensor assembly 122 may be inside of the shoe 120, or may be embedded within the material that forms the shoe upper or the shoe sole.

The spacing s between the sensors 22 is suitable for functioning of the multiple sensors in detecting objects with which a subject wearing the shoe may collide. For example, s may be in a range of approximately 0.5-2.5 centimeters (cm). Although s is shown as being approximately uniform along the entire length of the sensor assembly 22, s may be non-uniform. For example, the sensors 22 may be closer together at a front 125 of the shoe 120 than they are along the sides [126] or at the back 128 of the shoe—the sensors 22 along the back of the shoe may detect an object as the subject is walking backward, or may detect an object that is moving toward the subject from behind.

Furthermore, the notifier 38 may have portions 130 that are distributed along the length of the sensor assembly 122. For example, these distributed notifier portions 130 may be LEDs, and to recommend that a subject wearing the shoe 120 be cautious, or take evasive action, to avoid a collision with an object to the right of the shoe, the determiner 36 may signal the notifier 38 to flash one or more of the LEDs 130 on the right side of the shoe. Similarly, to recommend that a subject wearing the shoe 120 be cautious, or take evasive action, to avoid a collision with an object in front of, or to the left of, the shoe, the determiner 36 may signal the notifier 38 to flash one or more of the LEDs 130 on the front of, or on the left side of, the shoe.

Alternatively, the notifier portions 130 may be configured to elicit from the subject a reflexive response that causes the subject to avoid a potential collision with a detected object. For example, if the subject is walking toward, or up, stairs, and the determiner 36 determines that the subject may stub his toe on a stair, then the determiner may signal the notifier 38 to cause one or more of the notifier portions 130 to vibrate in a manner that causes the subject to reflexively lift his foot higher as he steps toward, and ultimately upon, the stair.

In another example, the distributed notifier portions 130 may be mini lasers. To recommend that a subject wearing the shoe 120 take evasive action to avoid a collision with an object to the right of the shoe, the determiner 36 may signal the notifier 38 to activate a laser 130 on the left side of the shoe to "point" in the direction (here left) in which the subject should veer, or otherwise move, to avoid the potential collision.

Although only one shoe 120 is described, a subject may wear two shoes 120, one on each foot. The sensor assembly 122 on the right shoe 120 may be disposed along the front 125, the right (outer) side 126, and the back 128 of the right shoe, and the sensor assembly 122 on the left shoe may be disposed along the front 125, the left (outer) side 126, and the back 128 of the left shoe. This configuration omits portions of the sensor assembly 122 along the inner sides of the left and right shoes 120, because the sensor-array portions along the outer sides of the left and right shoes may be better able to detect objects without interference from the other shoe as the shoes pass by one another while the subject is walking. Furthermore, in addition to including respective sensors 22, each shoe 120 may include a respective determiner-notifier module 26 (FIG. 2), where the determiner-notifier modules are configured to communicate with one another via the respective associated ports 30 (FIG. 2). For example, if the sensors 22 of both sensor assemblies 122 on both shoes 120 detect an object 42, then the determiner-notifier modules 26 may communicate with one another to determine which shoe's notifier portions 130 to use to generate a warning or other notification. Alternatively, the shoes 120 may share a single determiner-notifier module 26, which may be disposed on one of the shoes, on the subject remote from the shoes, or remote from the subject.

Still referring to FIG. 11, alternate embodiments of the shoe 120 are contemplated. For example, although described as being disposed along the periphery of the shoe 120, the sensor assembly 122 may be disposed on (or in) a tongue 132, laces 134, or other portions of the shoe. Furthermore, although a single sensor assembly 122 is described as being attached to the shoe 120, multiple sensor assemblys may be attached to the shoe. In addition, although described as being LEDs or lasers, the distributed notifier portions 130 may be configured to generate a noise as a notification; for example, the notifier portions may be, or include, piezo-electric buzzers, "whistling" devices, or voice-generating devices that can "speak" recommendations, warnings, or other notifications. In addition, although described as including the sensors 22 and other components of the device 20 of FIG. 2, the sensor assembly 122 may include the sensors and other components of one or more of the devices 90, 92, 110, and 116 of FIGS. 2 and, 7-10, or one or more portions of one of more of these devices, according to an embodiment. Furthermore, if the sensor assembly 122 includes the device 110 of FIG. 9, then the base module 96 (not shown in FIG. 11) may be disposed on the shoe 120 or may be disposed remote from the shoe, such as in the pocket of the subject (not shown in FIG. 11) who is wearing the shoe.

FIG. 12 is a side view of a system, here a sock 140, which includes a sensor assembly 142, according to an embodiment. Incorporating the sensor assembly within the sock 140 may provide object detection and potential-collision notification even when a subject (not shown in FIG. 12) is not wearing shoes.

The sensor assembly 142 may be similar to the sensor assembly 122 of FIG. 11.

Furthermore, the sensor assembly 142 is disposed around some, or all, of the periphery of the sock 140 (the sensor assembly is disposed around the entire periphery of the sock in FIG. 12), and may be integral with, or stitched to, the sock 140, or the sensor assembly may be attached to the sock with adhesive (removable or non-removable) or Velcro® (removable). Alternatively, all or part of the sensor assembly 122 may be inside of the sock 140, or embedded within or integral to the material that forms the sock, for example using conformable electronics or electronic thread or other conductive thread. And although described as being disposed along an upper portion 144 of the sock 140, the sensor assembly 142 may be disposed along a lower portion 146 of the sock.

Still referring to FIG. 12, alternate embodiments of the sock 140 are contemplated. For example, although a single sensor assembly 142 is described as being attached to the sock 140, multiple sensor assemblies may be attached, or otherwise secured, to the sock.

FIG. 13 is a view of a system, here a piece of jewelry 150, such as an anklet, ankle bracelet, or wrist bracelet, which includes a sensor assembly 152, according to an embodiment. Incorporating the sensor assembly 152 with the jewelry piece 150 may provide a subject (not shown in FIG. 13) with object detection and notification even when he/she is not wearing shoes or socks.

The sensor assembly 152 may be similar to the sensor assembly 122 of FIG. 11.

Furthermore, the sensor assembly 152 is disposed around some, or all, of the periphery of the jewelry piece 150, and the sensor assembly may be attached to the jewelry piece with adhesive (removable or non-removable) or Velcro® (removable). Or, the sensor assembly 152 may be located inside of the jewelry piece 150, or embedded within or integral to the material that forms the piece.

Still referring to FIG. 13, alternate embodiments of the jewelry piece 150 are contemplated. For example, although a single sensor assembly 152 is described as being attached to the jewelry piece 150, multiple sensor assemblies may be attached to the jewelry piece. Furthermore, other examples of the jewelry piece 150 include necklaces and earrings, and accessories such as belts and headbands.

FIG. 14 is a view of a system, here a pair of pants 160, which includes a sensor assembly 162, according to an embodiment. Incorporating the sensor assembly 162 with the pants 160 may provide object detection and notification for a subject even when he/she is not wearing socks or shoes.

The sensor assembly 162 may be similar to the sensor assembly 122 of FIG. 12.

Furthermore, the sensor assembly 162 is disposed along a portion of a pant leg 164, and may be integral with, or stitched to, the pants 160, or the sensor assembly may be attached to the pants with adhesive (removable or non-removable) or Velcro® (removable). Alternatively, the sensor assembly 162 may be inside of the pants 160, or buried within the material that forms the pants. And although described as being disposed along a portion of the pant leg 164, the sensor assembly 162 may be disposed along any other suitable portion of the pants 160, such as partially or fully around a waist 166 or cuff 168.

Still referring to FIG. 14, alternate embodiments of the pants 160 are contemplated. For example, although a single sensor assembly 162 is described as being attached to the pants 160, multiple sensor assemblies may be attached to the pants.

FIG. 15 is a view of a system, here a shirt 170, which includes a sensor assembly 172, according to an embodiment. Incorporating the sensor assembly 172 with the shirt 170 may provide object detection and avoidance for a subject even when he/she is not wearing socks or shoes.

The sensor assembly 172 may be similar to the sensor assembly 122 of FIG. 12.

Furthermore, the sensor assembly 172 is disposed along a portion of a waist 174, and may be integral with, or stitched to, the shirt 170, or the sensor assembly may be attached to the shirt with adhesive (removable or non-removable) or Velcro® (removable). Alternatively, the sensor assembly 172 may be inside of the shirt 170, or buried within the material that forms the shirt. And although described as being disposed along a portion of the shirt waste 174, the sensor assembly 172 may be disposed along any other suitable portion of the shirt 170, such as partially or fully around a sleeve 176 or a neck 178.

Still referring to FIG. 15, alternate embodiments of the shirt 170 are contemplated. For example, although a single sensor assembly 172 is described as being attached to the shirt 170, multiple sensor assemblies may be attached to the shirt.

Figure 16:
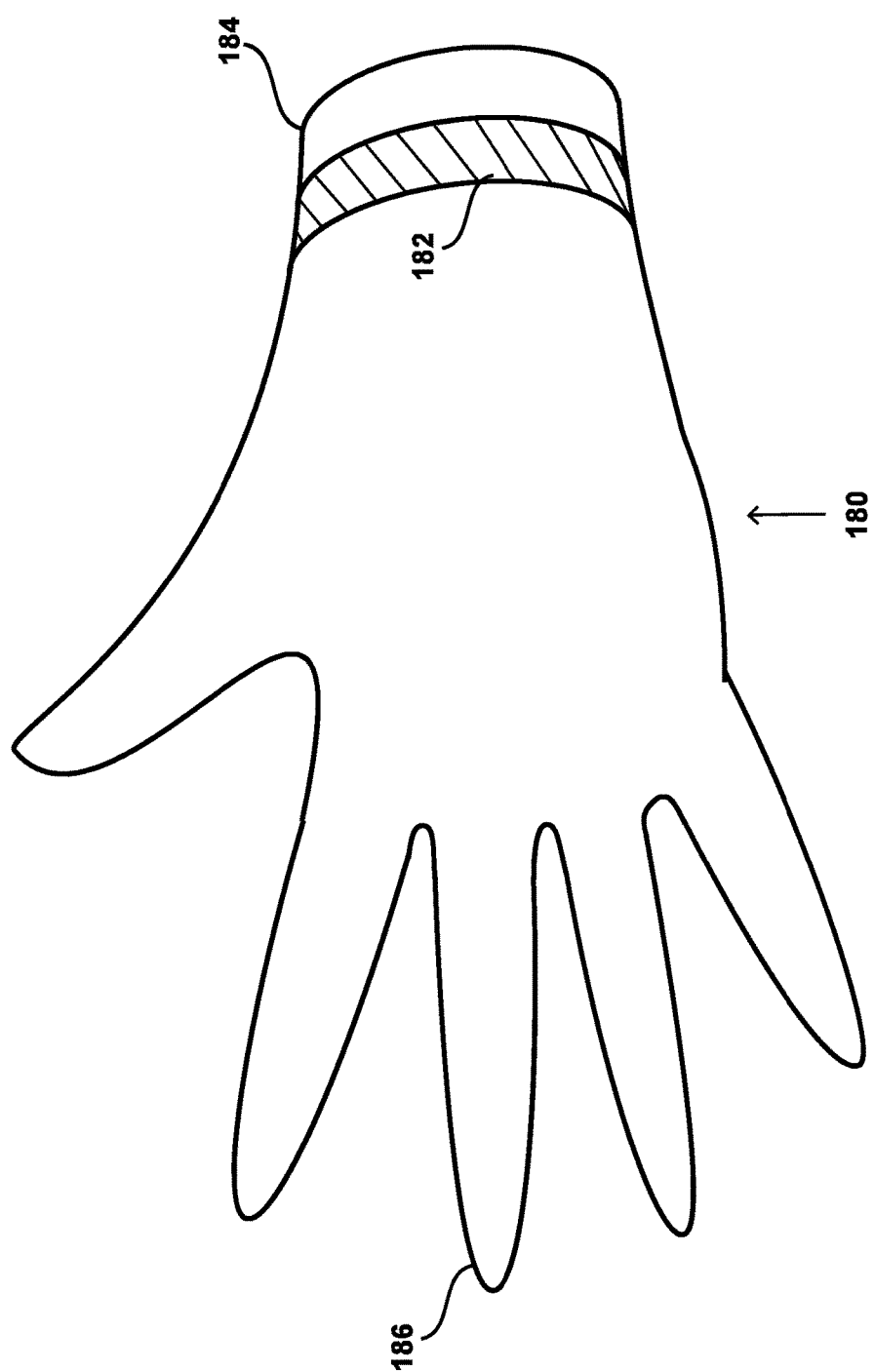
FIG. 16 is a view of a system that includes a glove and a device of one or more of FIGS. 2 and 7-10, according to an embodiment.

FIG. 16 is a side view of a system, here a glove 180, which includes a sensor assembly 182, according to an embodiment. Incorporating the sensor assembly 182 with the glove 180 may provide object detection and potential-collision notification regarding a potential collision between an object (e.g., a door handle, door jamb) and a subject's hand.

The sensor assembly 182 may be similar to the sensor assembly 122 of FIG. 11.

Furthermore, the sensor assembly 182 is disposed around some, or all, of the cuff 184 of the glove 180 (the sensor assembly is disposed around the entire cuff of the glove in FIG. 16), and may be integral with, or stitched to, the glove, or the sensor assembly may be attached to the glove with adhesive (removable or non-removable) or Velcro® (removable). Alternatively, the sensor assembly 182 may be inside of the glove 180, or embedded within or integral to the material that forms the glove. And although described as being disposed along a cuff 184 of the glove 180, the sensor assembly 182 may be disposed along or around a finger 186 of the glove.

Still referring to FIG. 16, alternate embodiments of the glove 180 are contemplated. For example, although a single sensor assembly 182 is described as being attached to the glove 180, multiple sensor assemblies may be attached, or otherwise secured, to the glove. Furthermore, the glove 180 may be another form of hand covering like a mitten.

FIG. 17 is a view of a system, here a hat 190, which includes a sensor assembly 192, according to an embodiment. Incorporating the sensor assembly 192 with the hat 190 may provide object detection and avoidance for a subject even when he/she is not wearing socks or shoes. For example, the sensor assembly 192 may include, e.g., as the sensors 22, one or more image-capture devices/sensors that capture images of a swath of the surface on which a subject is walking (the swath may be in front of, to one or both sides of, to the rear of, or partially or fully around the subject). The determiner-notifier module 26 (FIG. 2) may analyze the images to determine if the subject's feet may potentially collide with a detected object, and warn the subject if at least one of the subject's feet may collide with the detected object. An embodiment of such a procedure is described below in conjunction with FIGS. 18-19. The sensor assembly 192 may be similar to the sensor assembly 122 of FIG. 11 where the sensors 22 are image-capture sensors.

Furthermore, the sensor assembly 192 is disposed partially, or fully, around a head-covering portion 194, and may be integral with, or stitched to, the hat 190, or the sensor assembly may be attached to the hat with adhesive (removable or non-removable) or Velcro® (removable). Alternatively, the sensor assembly 192 may be inside of the hat 190, or buried within the material that forms the hat. And although described as being disposed along a portion of the head-covering portion 194, the sensor assembly 192 may be disposed along any other suitable portion of the cap 190, such on, in, or under a visor (not shown in FIG. 17) of the cap.

Still referring to FIG. 17, alternate embodiments of the hat 190 are contemplated. For example, although a single sensor assembly 192 is described as being attached to the hat 190, multiple sensor assemblies may be attached to the hat.

Referring to FIGS. 11-17, although the sensor assemblies 122, 142, 152, 162, 172, 182, and 192 are described as being attached to a shoe 120, sock 140, jewelry piece 150, pants 160, shirt 170, glove 180, and hat 190, one or more sensor assemblies may be attached to any other item that may be worn by, attached to, implanted in, or otherwise carried by a subject.

FIG. 18 is a diagram of a subject 40 wearing the hat 190 of FIG. 17, according to an embodiment.

Figure 19:
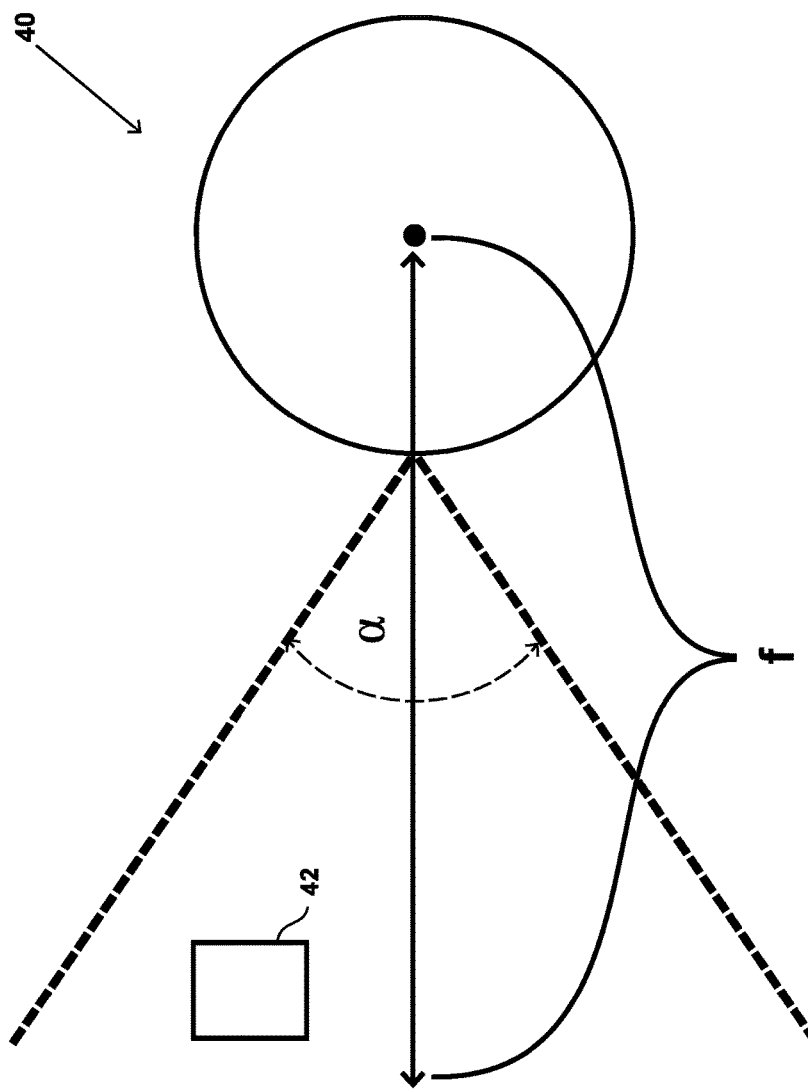
FIG. 19 is a top view of the human subject of FIG. 18 wearing the hat of FIG. 17, according to an embodiment.

FIG. 19 is a top view of the subject 40 and hat 190 of FIG. 17, according to an embodiment.

Referring to FIGS. 17-19, operation of the hat 190 is described, according to an embodiment in which the sensors 22 include one or more image-capture sensors.

While the subject 40 is walking or running, the one or more image-capture sensors 22 of the sensor assembly 192 acquire information representative of images of a swath or region 200 of a surface 202 on which the subject is walking or running. The information representative of the images may include electronic signals that represent properties (e.g., luminance, chrominance) of pixels of the images. Furthermore, the information representative of the images may include electronic signals that represent emitted or reflected or otherwise redirected (e.g., emitted, reflected or otherwise redirected by an object) energy in the form of, e.g., light, heat, or sound.

The region 200 may encompass any part, or the entirety of, the periphery around the subject 40, and may extend out a distance f from the subject. For example, the region 200 may encompass a lateral range of, for example, approximately $\alpha=90$ degrees in front of the subject, and f may be, for example, in an approximate range of 0-5 meters.

The determiner 36 (FIG. 2) constructs from the image information received from the one or more image-capture sensors representations (e.g., pixel maps) of the images, and analyzes these image representations to identify one or more objects 42 within the region 200 and to determine whether a body portion, e.g., one or both feet 204, of the subject 40 may contact one or more detected objects as described above in conjunction with FIGS. 2-6.

And if the determiner 36 determines that the body portion of the subject 40 may contact one or more objects 42, it orders the notifier 38 to notify the subject as described above in conjunction with FIGS. 2-6.

Still referring to FIGS. 17-19, other embodiments are contemplated. For example, although the sensor assembly 192 is described as being disposed on a hat 190, the sensor assembly may be disposed elsewhere, such as around a waist 206, on a chest 208, or on one or both arms 210 of the subject 40.

FIGS. 20-25 are diagrams of sensors that may be used as the sensors 22 of FIGS. 2 and 7-10, according to embodiments. For example, any one or more of these sensors may be disposed on a shoe such as the shoe 120 of FIG. 11 (e.g., on the front tip of the shoe).

FIG. 20 is a diagram of a passive sensor 220 as it senses an object 42, according to an embodiment. Examples of the passive sensor 220 include an image-capture sensor, an infrared sensor, and a microphone.

The passive sensor 220 is configured to detect an energy wave 222 (e.g., electromagnetic wave or sound wave) that emanates from the object 42. For example, the energy wave 222 (e.g., infrared wave) may be generated and emitted by the object 42, or the energy wave (e.g., light wave) may be redirected by the object.

Furthermore, the passive sensor 220 may include a lens or other structure 224 to collect and focus the energy wave 222, and may be able to discern the angle $\alpha$ at which the sensor receives the energy wave (e.g., $\alpha=90°$ as shown in FIG. 20).

Moreover, the passive sensor 220 may be configured to collect data that is sufficient to range the object 42 in one of several ways. For example, the sensor 220 may sense the energy wave 222 emanating from the object 42 from multiple different spatial locations at respective times as the subject (not shown in FIG. 20) and object move relative to one another; based on the distances between these locations and the respective angles $\alpha$, the determiner-notifier module 26 (FIG. 2) may triangulate the position of the object. Or, multiple sensors 220 at different spatial locations (e.g., along a side of the shoe 120 of FIG. 11) may sense, approximately simultaneously, respective portions of an energy wave emanating from the object 42; based on the distances between these locations and the respective angles $\alpha$, the determiner-notifier module 26 may triangulate the position of the object.

Still referring to FIG. 20, alternate embodiments of the passive sensor 220 are contemplated. For example, although described as having a cylindrical shape, the sensor 220 may have any suitable shape. Furthermore, although described as sensing one object 42 at a time, the sensor 220 may sense multiple objects simultaneously by simultaneously discerning multiple angles $\alpha$.

FIG. 21 is a diagram of a mono-transmit-receive sensor 230 as it senses an object 42, according to an embodiment. Examples the mono-transmit-receive sensor 230 include an ultrasound sensor, an optical sensor, radar, and sonar.

The mono-transmit-receive sensor 230 is configured to emit an energy wave 232 (e.g., electromagnetic wave or ultrasonic wave) toward the object 42 during a first time period $t_1$, and is configured to sense a portion 234 of the energy wave 232 redirected by the object during a second time period $t_2$.

The mono-transmit-receive sensor 230 may include a lens or other structure 236 for focusing the transmitted energy wave 232, and for collecting and focusing the redirected portion 234 of the energy wave. The sensor 230 may also be able to discern the angle $\alpha$ at which the sensor receives the redirected portion 234 of the energy wave 230 (e.g., $\alpha=90°$).

The sensor 230 may be configured to collect data that is sufficient to range the object 42 in one of several ways.

For example, the sensor 230 may generate the energy wave 232 from a first set of multiple different spatial locations at first respective times, and sense the portion 234 of the energy wave redirected by the object 42 from a second set of multiple different spatial locations at second respective times as the subject (not shown in FIG. 21) and object move relative to one another; based on the distances between the first locations and the respective angles $\alpha$, the determiner-notifier module 26 (FIG. 2) may triangulate the position of the object.

Or, multiple sensors 230 at different first spatial locations (e.g., along a side of the shoe 120 of FIG. 11) may generate a first set of energy waves 232 approximately simultaneously, and later sense, approximately simultaneously, respective portions 234 of the energy waves redirected by the object 42 at a set of respective second locations; based on the distances between the first locations and the respective angles $\alpha$, the determiner-notifier module 26 may triangulate the position of the object.

Alternatively, the determiner-notifier module 26 (FIG. 2) may range the object 42 by measuring an interval T between a point of the transmitting period $t_1$ and the same relative point of the receiving period $t_2$, and by determining the distance D from the sensor 22 to the object 42 according to the following equation:

$$D = R \cdot T \tag{1}$$

where R is the speed of propagation of the energy wave 232 in air. For example, such a technique may be used when the sensor 230 is an ultrasonic sensor or an infrared sensor, and may be similar to one or more ranging techniques that cameras use for autofocus.

Still referring to FIG. 21, alternate embodiments of the mono-transmit-receive sensor 230 are contemplated. For example, although described as having a cylindrical shape, the sensor 230 may have any suitable shape. Furthermore, although described as sensing one object 42 at a time, the sensor 230 may sense multiple objects simultaneously by discerning multiple angles α simultaneously, or by noting the different times at which it receives energy-wave portions 234 redirected by respective objects 42 relative to a same reference time.

Figure 22:
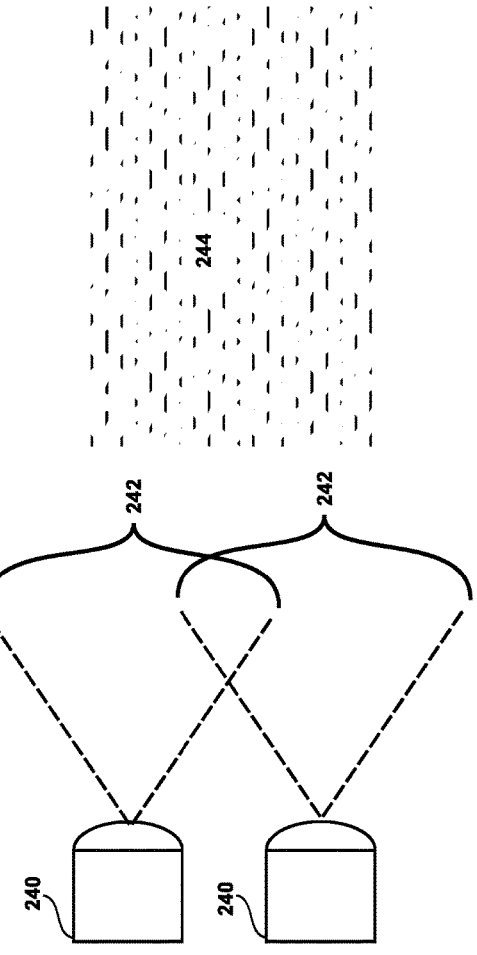
FIG. 22 is a diagram of sensors positioned to have overlapping sensing lobes, according to an embodiment.

FIG. 22 is a diagram of two sensors 240 having overlapping sensing (energy-wave-receiving) lobes 242, according to an embodiment. Placing the sensors 240 so that they have overlapping sensing lobes 242 may prevent detection "holes" in an object-detection region 244, which may be, for example, from between 0-5 meters from the sensors. For example, each of the sensors 240 may be similar to the sensor 220 of FIG. 20 or to the sensor 230 of FIG. 21.

FIG. 23 is a diagram of a dual-transmit-receive sensor 250 as it senses an object 42, according to an embodiment. Examples of the dual-transmit-receive sensor 250 include an ultrasound sensor, an optical sensor, and sonar.

The dual-transmit-receive sensor 250 includes a transmitter 252, which is configured to emit an energy wave 254 (e.g., electromagnetic wave or ultrasonic wave) toward the object 42, and a receiver 256 configured to sense a portion 258 of the energy wave 254 redirected by the object.

The transmitter 252 and the receiver 256 each may include a respective lens or other structure 259 to focus the transmitted energy wave 244, and to collect and focus the redirected portion 258 of the energy wave, respectively. The receiver 246 may also be able to discern the angle α at which the receiver receives the redirected portion 258 of the energy wave 254 (e.g., α=90°).

The dual-transmit-receive sensor 250 may be configured to collect data that is sufficient to range the object 42 in one of several ways. For example, the transmitter 252 may generate the energy wave 254 from a first set of multiple different spatial locations at first respective times, and the receiver 246 may sense the portion 248 of the energy wave redirected by the object 42 from a second set of multiple different spatial locations at second respective times as the subject (not shown in FIG. 23) and object move relative to one another; based on the distances between these second locations and the respective angles α, the determiner-notifier module 26 (FIG. 2) may triangulate the position of the object. Or, the transmitters 252 of multiple dual-transmit-receive sensors 250 at a first set of different spatial locations (e.g., along a side of the shoe 120 of FIG. 11) may generate a first set of energy waves 254 approximately simultaneously, and the receivers 246 may later sense, approximately simultaneously, the portions 248 of the respective energy waves redirected by the object 42 at a second set of respective locations; based on the distances between the first locations and the respective angles α, the determiner-notifier module 26 may triangulate the position of the object. In addition, the determiner-notifier 26 may range the object 42 by measuring an interval T between a point of a period $t_1$ during which the transmitter 252 emits the energy wave 244 and the same relative point of a period $t_2$ during which the receiver 256 receives the redirected portion 258 of the energy wave; then, the determiner-notifier 26 determines the distance D from the sensor 250 to the object 42 according to equation (1) above.

Still referring to FIG. 23, alternate embodiments of the dual-transmit-receive sensor 250 are contemplated. For example, although described as having a cylindrical shape, the transmitter 252 and receiver 256 may have any suitable shape. Furthermore, although described as sensing one object 42 at a time, the receiver 256 may sense multiple objects approximately simultaneously by receiving portions 258 of the energy wave 254 redirected by different objects.

Referring to FIGS. 20-23, other types of sensors that may take the form of the sensors described in conjunction with these FIGS. include a range sensor, proximity sensor, RFID sensor (also called an RFID tag), thermal sensor, chemical sensor, multi-spectral sensor (also called a hyper-spectral sensor), and electromagnetic-radiation sensor. For example, a thermal sensor may detect an object in response to heat generated by the object, or may warn that an object is at an inappropriate temperature (e.g., too hot or too cold), for a person to contact—this latter feature may be useful for a person who has lost the ability to sense temperature in at least one body part. Furthermore, a chemical sensor may detect an object by its chemical makeup or chemicals it emits (e.g., a chemical bar code) or sheds, or may warn that an object has an inappropriate composition (e.g., caustic, allergen) for a person to contact—this latter feature may be useful for a person who has lost the ability to sense that a harmful composition (e.g., acid) is contacting at least one body part.

Figure 24:
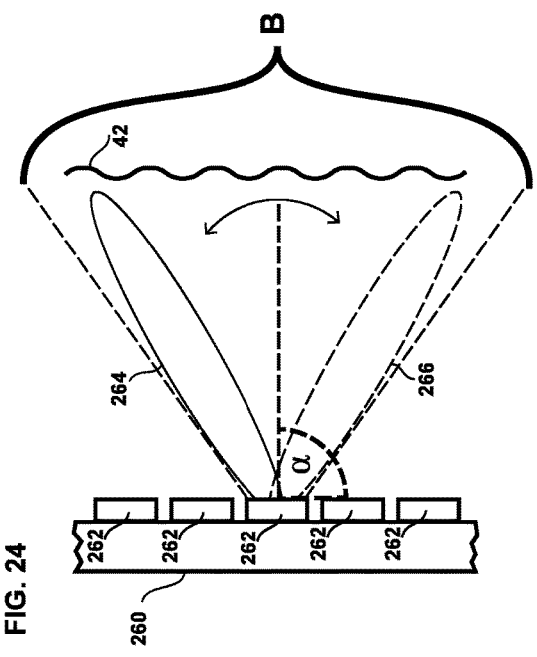
FIG. 24 is a diagram of an active phased-array sensor transmitting a signal at one time, and sensing a portion of the signal redirected by an object at a later time, according to an embodiment.

FIG. 24 is a diagram of a phased-array sensor 260 sensing an object 42, according to an embodiment. Examples the phased-array sensor 260 include a phased-array radar sensor and a phased-array sonar sensor.

The phased-array sensor 260 includes a number of transmit-receive elements 262.

Furthermore, the phased-array sensor 260 is configured to generate and to steer a beam 264 (shown in solid line) of transmitted energy waves to scan for an object 42—each element 262 generates a respective energy wave—and also is configured to steer a receive lobe 266 (shown in dashed line) to detect the object; for example, the energy waves may be radar waves or acoustic waves. The sensor 260 is configured to steer the beams 264 and the lobe 266 by appropriately setting the respective gain and phase of each element 262.

In operation, the sensor 260 first steers the transmit beam 264 over a suitable angle β during a time period $t_1$.

Next, the sensor 260 steers the receive lobe 266 back and forth over the angle β during a time period $t_2$.

In response to detecting, within the receive lobe 266, a portion of the transmit beam 264 redirected by the object 42, the determiner-notifier module 26 (FIG. 2) measures the interval T from when the transmit beam had the same angle α as the receive lobe does while detecting the redirected portion of the transmit beam. Then, the determiner-notifier module 26 determines the distance D from the sensor 22 to the object 42 according to equation (1) above.

Furthermore, the determiner-notifier module 26 may determine the direction of the detected object 42 relative to the phased-array sensor 260, and thus relative to the subject (not shown in FIG. 24), in response to the angle α of the receive lobe 266.

Still referring to FIG. 24, alternate embodiments of the phased-array sensor 260 are contemplated. For example, although described as being flat, the sensor 260 may be curved, or otherwise not flat. Furthermore, although described as sensing one object 42 at a time, the sensor 260 may sense multiple objects approximately simultaneously as a result of scanning the transmit beam 264 and the receive lobe 266.

Figure 25:
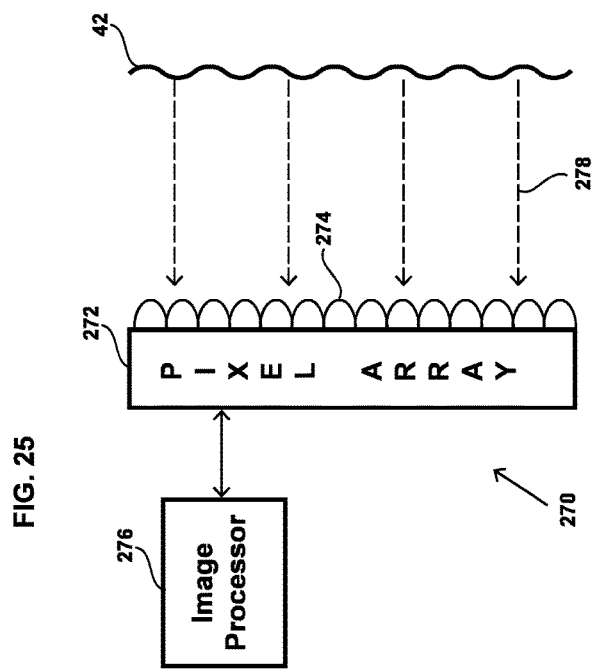
FIG. 25 is a diagram of an image-capture sensor sensing electromagnetic energy, such as light, redirected by an object, according to an embodiment.

FIG. 25 is a diagram of an image-capture sensor 270 (also called an image-capture device), which may be, or which may be used as, a sensor 22 of FIG. 2, according to an embodiment. Examples of the image-capture sensor 270 include an electronic camera (light images), video recorder (sequence of light images), thermographic camera (heat images), thermal imager (heat images), and sonographic camera (sound or other vibration images).

The image-capture sensor 270 includes a pixel array 272, microlenses 274 disposed over the pixel array, and an image processor 276. For example, the image-capture sensor 270 may be a camera that is configured to capture visible-light images, or infrared images for use in the dark.

In operation, the object 42 redirects electromagnetic waves 278 toward the microlenses 274. The electromagnetic waves 278 may include light in the visible spectrum, or electromagnetic waves (e.g., infrared) outside of the visible spectrum.

Next, the microlenses 274 focus the waves 278 onto the elements of the pixel array 272, which provides pixel information (e.g., voltage or current levels) to the image processor 276.

Then, in response to the pixel information, the processor 276 generates information (e.g., digital values) that represents an image (e.g., a two-dimensional or three-dimensional image) of the object 42. For example, the information may include, e.g., the luminance values of each pixel of the image, the chrominance values of each pixel of the image, a histogram of the image, or the edges of objects within the image.

Still referring to FIG. 25, following are some of the embodiments and uses contemplated for the image-capture sensor 270.

For example, in a manner similar to that described above in conjunction with FIGS. 17-19, a subject may wear the image-capture sensor 270 on his/her torso or head such that the device is pointed downward to monitor a region near the subject's feet for obstacles. The "view" of the image-capture sensor 270 may include, none, one, or both of the subject's feet, an actual or potential path in front of one or both of the feet, or an area near one or both of the feet, for example a 180-degree region around a foot.

Furthermore, the image processor 276, or another portion of the image-capture sensor 270, may be configured to motion-stabilize the device or a captured image, in hardware or software, to maintain an approximately steady field of view; for example, the device may include gyro-stabilized optics or processor-implemented image stabilization.

In addition, the image-capture sensor 270 may be configured to capture and to generate three-dimensional images, e.g., for stereoscopic "vision" or to obtain and to generate a two-dimensional image plus range.

Furthermore, the image-capture sensor 270 may be configured to capture and to generate one image at a time, or to capture a stream of images and to generate a video sequence of the captured images.

Still referring to FIG. 25, alternate embodiments of the image-capture sensor 270 are contemplated. For example, although not described above, the sensor 270 may include a lens or other optical train disposed in front of the microlenses 274.

Figure 26:
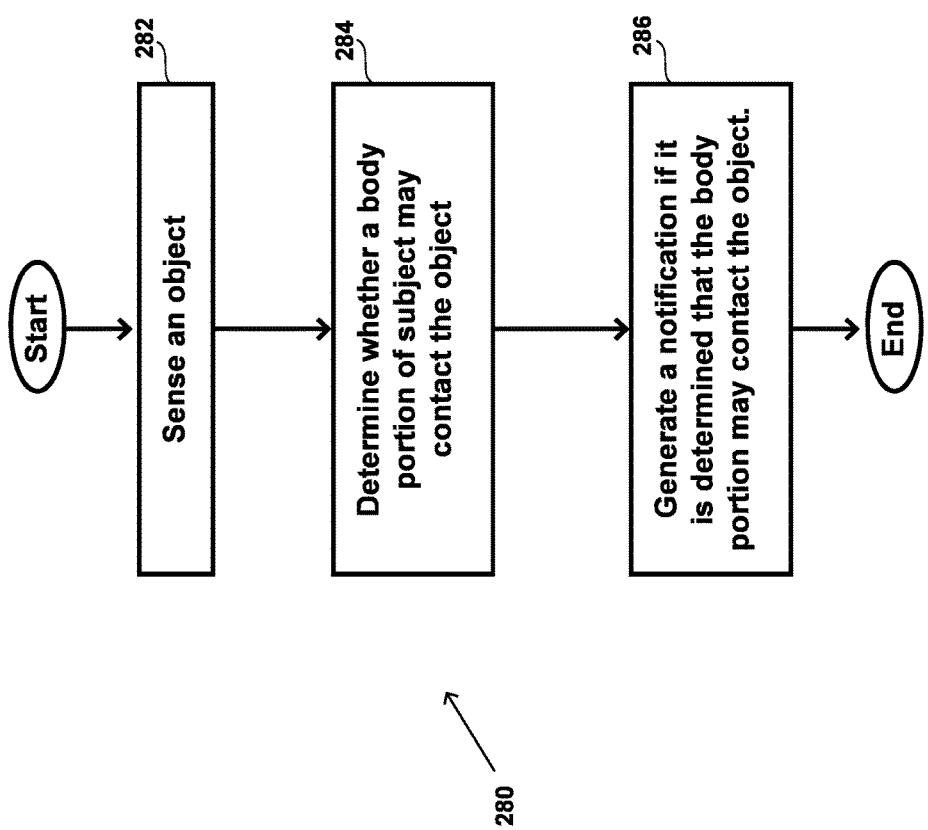
FIG. 26 is a flow diagram of a sensing and notification method, according to an embodiment.

FIG. 26 is a flow diagram 280 of a method that any one of the items of FIGS. 11-17 may implement, where the item can include any one or more of the devices of FIGS. 2 and 7-10 and any one or more of the sensors of FIGS. 20-25, according to an embodiment. For purposes of explanation, the method is described in conjunction with the shoe 120 of FIG. 11 and the device 20 of FIG. 2, it being understood that the method could be similar for any other item and for any other device.

Referring to FIGS. 2-4, 11, and 26, at a step 282, one or more of the enabled sensors 22 detect an object 42, and generate sensor information related to the object.

At a step 284, the determiner-notifier module 26 determines, in response to the sensor information related to the object 42, whether a body portion of the subject 40 may contact the object.

Then, at a step 286, the determiner-notifier module 26 generates a notification if the detector determines that the body portion may contact the object. The notification may recommend to the subject 40 an action, such as slowing down, shortening his/her stride, or an evasive maneuver, that will prevent, or at least reduce the chances of, a collision between the subject and the object 42.

Referring to FIG. 26, alternate embodiments of the method described in conjunction with the flow diagram 280 are contemplated. For example, the method may include additional or fewer steps, and the described steps may be performed serially, in parallel, or in an order different from the order described.

Figure 27:
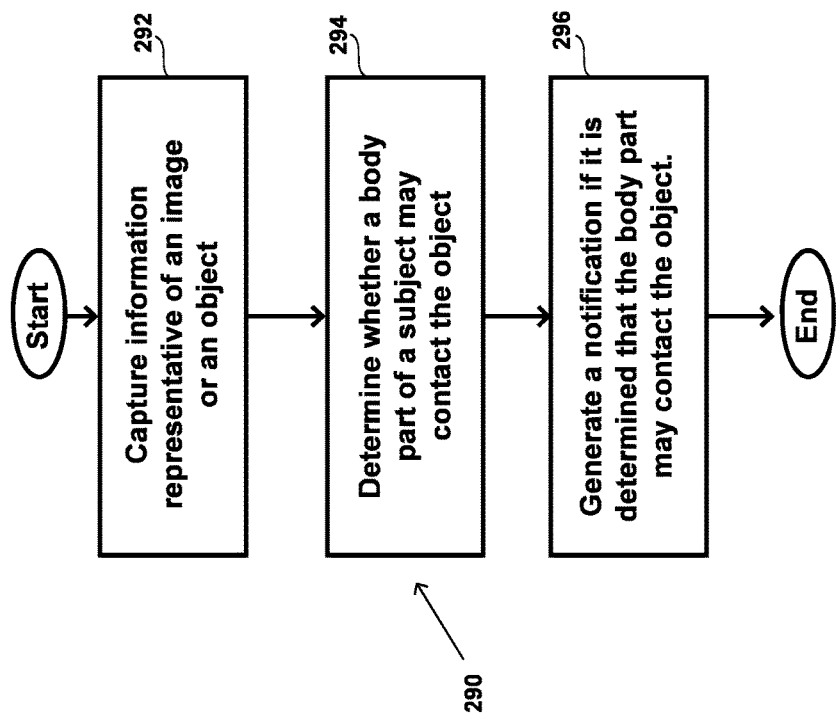
FIG. 27 is a flow diagram of a sensing and notification method, according to another embodiment.

FIG. 27 is a flow diagram 290 of a method that any one of the items of FIGS. 11-17 may implement, where the item can include any one or more of the devices of FIGS. 2 and 7-10, and where at least one of the sensors 22 is, or is replaced by, the image-capture sensor 270 of FIG. 25, according to an embodiment. For purposes of explanation, the method is described in conjunction with the shoe 120 of FIG. 11 and the device 20 of FIG. 2 with at least one sensor 22 being an image-capture sensor 270, it being understood that the method could be similar for any other item and device.

Referring to FIGS. 2-4, 11, 25, and 27, at a step 292, one or more enabled image-capture sensors 270 captures information representative of an image of the object 42. For example, at least one of the enabled image-capture sensors 270 may include a camera.

Next, at a step 294, the determiner-notifier module 26 determines, in response to the image information related to the object 42, whether a body portion of the subject 40 may contact the object.

Then, at a step 296, the determiner-notifier module 26 generates a notification if the determiner-notifier module determines that the body portion of the subject 40 may contact the object 42. The notification may recommend to the subject 40 an action, such as slowing down, shortening his/her stride, or an evasive maneuver, that will prevent, or at least reduce the chances of, a collision between the subject and the object 42.

Referring to FIG. 27, alternate embodiments of the method described in conjunction with the flow diagram 290 are contemplated. For example, the method may include additional or fewer steps, and the described steps may be performed serially, in parallel, or in an order different from the order described.

Figure 28:
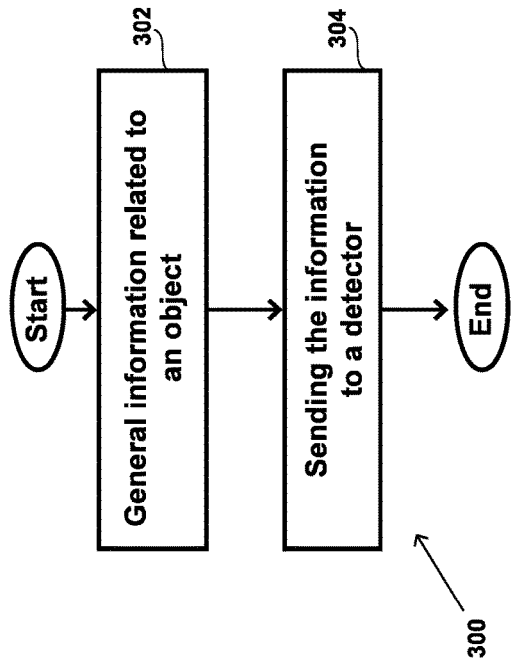
FIG. 28 is a flow diagram of a sensing method, according to an embodiment.

FIG. 28 is a flow diagram 300 of a method that any one of the items of FIGS. 11-17 may implement, where the item can include any one or more of the devices of FIGS. 2 and 7-10 and any one or more of the sensors of FIGS. 20-25, according to an embodiment. For purposes of explanation, the method is described in conjunction with the shoe 120 of FIG. 11 and the device 20 of FIG. 2, it being understood that the method could be similar for any other item and sensor system.

Referring to FIGS. 2-4, 11, and 26, at a step 302, one or more of the enabled ones of the sensors 22 detect an object 42, and generate information related to the object.

Next, at a step 304, the communicator 100 sends the information related to the object 42 to the determiner-notifier module 26. For example, the communicator 100 may transmit this information wirelessly to the determiner-notifier module 26.

Referring to FIG. 28, alternate embodiments of the method described in conjunction with the flow diagram 300 are contemplated. For example, the method may include additional or fewer steps, and the described steps may be performed serially, in parallel, or in an order different from the order described.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

While various aspects and embodiments have been disclosed herein, other aspects and embodiments will be apparent to those skilled in the art from the detailed description provided herein. The various aspects and embodiments disclosed herein are for purposes of illustration and are not intended to be limiting, with the true scope and spirit being indicated by the following claims.

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of the device, and any associated computing devices of the system operate as specific use computers for purposes of the claimed system, and not general use computers. In an embodiment, at least one associated computing device of the system operates as specific use computers for purposes of the claimed system, and not general use computers. In an embodiment, at least one of the associated computing devices of the system are hardwired with a specific ROM to instruct the at least one computing device. In an embodiment, one of skill in the art recognizes that the device and system effects an improvement at least in the technological field of object detection and collision avoidance.

What is claimed is:

1. An apparatus, comprising:
   at least one sensor configured to be worn on a body portion of a subject and to sense an object;
   a determiner configured to determine, in response to the at least one sensor, a trajectory of the subject as the subject is moving backward and whether the body portion will come within a threshold distance of the object if the trajectory remains unchanged; and
   a notifier configured to notify the subject, in response to the determiner determining that the body portion will come within the threshold distance of the object if the trajectory remains unchanged, of a direction to avoid to prevent the body portion from contacting the object.

2. The apparatus of claim 1 wherein the at least one sensor includes an array of sensors.

3. The apparatus of claim 1 wherein the at least one sensor is configured to sense an object that is located within a region in front of the body portion.

4. The apparatus of claim 1 wherein the at least one sensor is configured to sense an object that is located within a region that is peripheral to the body portion.

5. The apparatus of claim 1 wherein the at least one sensor includes sensors disposed along a periphery of the body portion.

6. The apparatus of claim 1 wherein the at least one sensor is configured to scan a region adjacent to the body portion.

7. The apparatus of claim 1 wherein the at least one sensor is configured to be attached to the subject.

8. The apparatus of claim 1 wherein the at least one sensor is configured to be part of a shoe.

9. The apparatus of claim 1 wherein the at least one sensor is configured to be attached to a shoe.

10. The apparatus of claim 1 wherein the determiner is configured to determine a change in the trajectory that the subject can make to prevent the body portion from contacting the object.

11. The apparatus of claim 1, further including a power source.

12. The apparatus of claim 1 wherein the at least one sensor is configured to sense an object that is located within a region behind the body portion.

13. The apparatus of claim 1 wherein the at least one sensor is configured to sense an object that is located within a region behind the subject.

14. An apparatus, comprising:
 means for sensing an object, the means for sensing wearable on a body portion of a subject;
 means for determining, in response to the means for sensing, a trajectory of the body portion as the body portion is moving backward;
 means for predicting whether the body portion will come within a threshold distance of the object if the trajectory remains unaltered; and
 means for notifying the subject, in response to the means for predicting that the body portion will come within the threshold distance of the object if the trajectory remains unaltered, that the body portion will come within the threshold distance of the object unless the trajectory is altered, and to alter the trajectory by changing a velocity of the body portion.

15. The apparatus of claim 14 wherein the means for determining and the means for predicting include a personal computing device.

16. The apparatus of claim 14 wherein the means for determining and the means for predicting are disposed on a personal computing device.

17. The apparatus of claim 14 wherein the means for determining includes means for determining whether the object is within the threshold distance from the means for sensing.

18. The apparatus of claim 14 wherein the means for determining includes means for determining whether the object is within the threshold distance from the body portion.

19. The apparatus of claim 14 wherein the means for determining includes means for determining a velocity of the body portion relative to the object.

20. The apparatus of claim 14 wherein the means for determining includes means for determining, in response to the means for sensing, the trajectory of the body portion as the subject is moving backward.

21. A method, comprising:
 sensing an object with at least one sensor being worn on a body portion of a subject;
 determining a trajectory of the subject as the subject is moving backward;
 predicting whether the subject will contact the sensed object if the trajectory remains unaltered; and
 in response to predicting that the subject will contact the object if the trajectory remains unaltered, notifying the subject to alter the trajectory by stopping to prevent the subject from contacting the object.

22. The method of claim 21 wherein the sensing includes sensing the object in response to an electromagnetic signal redirected by the object.

23. The method of claim 21 wherein the body portion includes a foot.

24. The method of claim 21, further comprising:
 determining a trajectory of the sensed object; and
 wherein the predicting includes predicting whether the subject will contact the object if the trajectory of the subject and the trajectory of the sensed object remain unaltered.

25. The method of claim 21, further comprising:
 determining a distance between the body portion and the sensed object; and
 wherein the predicting includes predicting, in response to the distance, whether the subject will contact the sensed object if the trajectory of the subject remains unaltered.

26. The method of claim 21 wherein the determining includes:
 determining a velocity of one of the subject and the sensed object; and
 wherein the predicting includes predicting, in response to the velocity, whether the subject will contact the sensed object if the trajectory of the subject remains unaltered.

27. The method of claim 21 wherein the determining includes:
 determining an acceleration of one of the subject and the sensed object; and
 wherein the predicting includes predicting, in response to the acceleration, whether the subject will contact the sensed object if the trajectory of the subject remains unaltered.

28. A system comprising:
 an item configured to be worn on a body portion of a subject;
 at least one first sensor configured to be disposed on the item and to sense an object;
 at least one second sensor configured to be disposed on the item and to sense information related to a position of the body portion;
 a determiner coupled to the at least one first sensor and to the at least one second sensor and configured to determine a trajectory of the body portion as the body portion is moving backward and whether the subject will come within a threshold distance of the object if the trajectory remains unchanged; and
 a notifier configured to notify the subject, in response to the determiner determining that the subject will come within the threshold distance of the object if the trajectory remains unchanged, to change the trajectory to prevent the subject from contacting the object.

29. The system of claim 28 wherein the item includes an article of clothing.

30. The system of claim 28 wherein the at least one first sensor is embedded within the item.

31. The system of claim 28 wherein the determiner is embedded within the item.

32. The system of claim 28 wherein the notifier is embedded within the item.

33. The system of claim 28 wherein the determiner is configured to determine, in response to the sensor, the trajectory of the body portion as the subject is moving backward.

34. A system comprising:
- an item wearable on a body portion of a subject;
- at least one sensor configured to be disposed on the item and to sense an object;
- a determiner configured to determine, in response to the at least one sensor, a trajectory of the body portion as the body portion is moving backward, and whether the subject will come within a threshold distance of the object if the trajectory remains unchanged; and
- a notifier configured to notify the subject, in response to the determiner determining that the subject will come within the threshold distance of the object if the trajectory remains unchanged, to change the trajectory to prevent the subject from contacting the object.

* * * * *